(12) United States Patent
Flieg et al.

(10) Patent No.: US 10,052,427 B2
(45) Date of Patent: Aug. 21, 2018

(54) FILTER DEVICE COMBINING BEADS AND FIBERS

(71) Applicant: GAMBRO LUNDIA AB, Lund (SE)

(72) Inventors: Ralf Flieg, Rangendingen (DE); Torsten Knoer, Burladingen (DE); Wolfgang Freudemann, Hechingen (DE); Mehmet Yildirim, Hechingen (DE); Martin Rempfer, Gomaringen (DE); Steffen Wagner, Messtetten (DE); Markus Storr, Filderstadt (DE)

(73) Assignee: GAMBRO LUNDIA AB, Lund (SE)

( * ) Notice: Subject to any disclaimer, the term of this patent is extended or adjusted under 35 U.S.C. 154(b) by 0 days.

(21) Appl. No.: 14/646,919

(22) PCT Filed: Nov. 5, 2013

(86) PCT No.: PCT/EP2013/073056
§ 371 (c)(1),
(2) Date: May 22, 2015

(87) PCT Pub. No.: WO2014/079680
PCT Pub. Date: May 30, 2014

(65) Prior Publication Data
US 2015/0320924 A1 Nov. 12, 2015

(30) Foreign Application Priority Data
Nov. 26, 2012 (EP) .................... 12194168

(51) Int. Cl.
*A61M 1/34* (2006.01)
*B01D 15/36* (2006.01)
(Continued)

(52) U.S. Cl.
CPC ........ *A61M 1/3475* (2014.02); *A61M 1/3472* (2013.01); *A61M 1/3486* (2014.02);
(Continued)

(58) Field of Classification Search
CPC .... A61M 1/16; A61M 1/1625; A61M 1/1627; A61M 1/1633; A61M 1/30; A61M 1/301;
(Continued)

(56) References Cited

U.S. PATENT DOCUMENTS 3,503,515 A    3/1970  Tomsic
4,675,384 A *  6/1987  Dromard ................ B01J 39/165
                                                 210/263

(Continued)

FOREIGN PATENT DOCUMENTS

EP    0341413        11/1989
EP    0 615 780 A1    9/1993
(Continued)

OTHER PUBLICATIONS

Gambro Lundia AB, "The Prismaflex eXeed system and the septeX set". May 5, 2009.*

(Continued)

*Primary Examiner* — Katherine Zalasky
*Assistant Examiner* — Benjamin L Lebron
(74) *Attorney, Agent, or Firm* — Barnes & Thornburg LLP

(57) ABSTRACT

A filter apparatus, a method for the manufacture of the filter apparatus, the use of the filter apparatus in medical, chemical and/or biotechnological applications, and an apparatus for use in the manufacture of the filter apparatus. The filter apparatus has a cylindrical housing and a plurality of hollow fibers. The hollow fibers are combined to form a bundle in the housing and are embedded and held in each case at the end sides in a molding compound. The filtrate space is filled with particles of a chemically or physically active substance.

19 Claims, 12 Drawing Sheets

(51) Int. Cl.

| | | |
|---|---|---|
| *B01D 61/00* | (2006.01) | |
| *B01J 20/28* | (2006.01) | |
| *B01D 15/12* | (2006.01) | |
| *B01D 69/08* | (2006.01) | |
| *B01D 15/32* | (2006.01) | |
| *B01D 15/26* | (2006.01) | |
| *B01D 15/38* | (2006.01) | |
| *B01D 63/02* | (2006.01) | |

(52) U.S. Cl.
CPC ......... *B01D 15/125* (2013.01); *B01D 15/265* (2013.01); *B01D 15/325* (2013.01); *B01D 15/362* (2013.01); *B01D 15/363* (2013.01); *B01D 15/3804* (2013.01); *B01D 61/00* (2013.01); *B01D 63/02* (2013.01); *B01D 63/021* (2013.01); *B01D 69/08* (2013.01); *B01J 20/28016* (2013.01); *A61M 1/3413* (2013.01); *B01D 2311/2626* (2013.01); *B01D 2313/40* (2013.01); *B01D 2325/20* (2013.01); *Y10T 29/4989* (2015.01)

(58) Field of Classification Search
CPC ...... A61M 1/303; A61M 1/34; A61M 1/3406; A61M 1/3417; A61M 1/3472; A61M 1/3475; A61M 1/3486; A61M 1/3413; B01D 15/3804; B01D 63/02; B01D 63/021; B01D 2311/2626; B01D 2313/40; B01D 61/24; B01D 61/28; B01D 61/30; B01D 15/20; B01D 15/206; B01D 15/22; B01D 15/125; B01D 15/265; B01D 15/325; B01D 15/362; B01D 15/363; B01D 61/00; B01D 69/08; B01D 2325/20; B01J 20/28016; Y10T 29/4989
See application file for complete search history.

(56) References Cited

U.S. PATENT DOCUMENTS

| | | | |
|---|---|---|---|
| 4,784,768 A | | 11/1988 | Mathieu |
| 6,497,675 B1 * | | 12/2002 | Davankov ............ A61M 1/3472 210/433.1 |
| 6,709,598 B1 | | 3/2004 | Pearl |
| 2002/0146413 A1 * | | 10/2002 | Brady ................... A01N 1/0278 424/140.1 |
| 2003/0111414 A1 | | 6/2003 | Baurmeister et al. |
| 2004/0035793 A1 * | | 2/2004 | Legendre, Jr. ..... C12N 15/1006 210/656 |
| 2004/0069710 A1 | | 4/2004 | Sirkar |
| 2004/0178136 A1 * | | 9/2004 | Taniguchi ............... B01D 63/02 210/321.79 |
| 2005/0015040 A1 | | 1/2005 | Wuepper et al. |
| 2005/0029193 A1 | | 2/2005 | Matson et al. |
| 2006/0099414 A1 * | | 5/2006 | Koops ................. B01D 67/0018 428/364 |
| 2008/0185322 A1 | | 8/2008 | Christmann et al. |
| 2009/0304677 A1 | | 12/2009 | Ichim et al. |
| 2010/0004588 A1 | | 1/2010 | Yeh et al. |
| 2011/0040228 A1 * | | 2/2011 | Radunsky ............ A61M 1/3413 604/5.04 |
| 2011/0094962 A1 | | 4/2011 | Heinrich et al. |
| 2011/0218512 A1 | | 9/2011 | Tullis et al. |
| 2012/0226258 A1 | | 9/2012 | Otto et al. |
| 2012/0305487 A1 | | 12/2012 | Beck et al. |

FOREIGN PATENT DOCUMENTS

| | | |
|---|---|---|
| EP | 1 257 333 | 8/2001 |
| EP | 1518870 | 3/2005 |
| EP | 1627941 | 2/2006 |
| EP | 1 875 956 A1 | 7/2006 |
| EP | 1 875 957 A1 | 7/2006 |
| EP | 1685862 | 8/2006 |
| EP | 2113298 | 11/2009 |
| EP | 2 380 610 A1 | 4/2010 |
| EP | 2281625 | 2/2011 |
| EP | 2 604 331 A1 | 12/2011 |
| EP | 2 735 360 A1 | 11/2012 |
| GB | 1470206 | 4/1977 |
| WO | 9108782 | 6/1991 |
| WO | 99/25726 A1 | 5/1999 |
| WO | 9925726 | 5/1999 |
| WO | 0067885 | 11/2000 |
| WO | 01/60477 A2 | 8/2001 |
| WO | 2004/003268 A1 | 1/2004 |
| WO | 2004014315 | 2/2004 |
| WO | 2004056460 | 7/2004 |
| WO | 2012/142180 A1 | 10/2012 |
| WO | 2012142180 | 10/2012 |

OTHER PUBLICATIONS

Boschetti de Fierro, A., et al. "Extended characteristics of a new class of membranes for blood purification: the high cut-off membranes", International Journal of Artificial Organs, vol. 36 No. 7, 455-463 (2013). Published online May 10, 2013.*
Burt, H.M., et al. "Ion-exchange resins as potential phosphate-binding agents for renal failure patients: effect on the physicochemical properties of resins on phosphate and bile salt binding," Journal of Pharmaceutical Sciences, vol. 76, No. 5, 379-383 (1987).*
Kirkland, J., et. al., "The art and science of forming packed analytical high-perforamnce liquid chromatography columns," Journal of Chromatography A, 1126, pp. 50-57 (2006).*
International Search Report from related WO 2014/079679 dated Feb. 4, 2014, 3 pages.
PCT International Search Report, International Application No. PCT/EP2013/073056, dated Dec. 20, 2013, 4 pages.
Aimar et al, A Contribution to the Translation of Retention Curves into Pore Size Distributions for Sieving Membranes, Journal of Membrane Science, 54, (1990), pp. 321-338.
Boldt, Use of Albumin: An Update, British Journal of Anaesthesia 104 (3): doi: 10.1093/bja/aep393, (2010), pp. 246-284.
Cardiovascular Implants and Extracorporeal Systems—Haemodialysers, Haemodiafilters, Haemofilters and Haemoconcentrators, International Standard, Reference No. ISO 8637, Third edition Jul. 1, 2010, 28 pages.
Stauber et al, MARS and Prometheus in Acute-on-Chronic Liver Failure: Toxin Elimination and Outcome, Transplantationsmedizin, (2010), 22. Jahrg., S., pp. 333-338.
Honore et al, Hemofiltration, Adsorption, Sieving and the Challenge of Sepsis Therapy Design, (2002), 4 pages, BioMed Central Ltd (Print ISSN 1364-8535; Online ISSN 1466-609X), http://ccforum.com/content/6/5/394.
Metallic powders—Determination of tap density (ISO 3953:2011); German version EN ISO 3953:2011, 2011, 9 pages.
PCT International Search Report, International Application No. PCT/EP2013/073045, dated Feb. 12, 2014, 3 pages.
PCT International Search Report, International Application No. PCT/EP2013/073058, dated Mar. 13, 2014, 6 pages.

* cited by examiner

FILTER DEVICE COMBINING BEADS AND FIBERS

CROSS REFERENCE TO RELATED APPLICATIONS

This application is the U.S. national phase of PCT/EP2013/073056 filed Nov. 5, 2013. PCT/EP2013/073056 claims priority under the Paris Convention to European patent application 12194168.6, filed Nov. 26, 2012. EP 12194168.6 and PCT/EP2013/073056 are hereby incorporated herein in their entireties by this reference.

TECHNICAL FIELD

The present invention relates to a filter apparatus having a cylindrical housing and a plurality of hollow fibers, with the hollow fibers being combined to form a bundle in the housing and being embedded and held in each case at the end sides in a moulding compound, and wherein the filtrate space is filled with particles of a chemically or physically active substance. The invention furthermore relates to a method for the manufacture of such filter apparatus, to the use of the filter apparatus in medical, chemical and/or biotechnological applications, and to an apparatus and its use for the manufacture of the filter apparatus.

DESCRIPTION OF THE RELATED ART

There are many applications existing which require the treatment of a fluid to change its composition, for example by removing an unwanted compound from such solution or collecting a compound from the solution. In some cases the fluid needs to be treated chemically, such as, for example, by a catalytic or enzymatic treatment of one or more of the substances contained in the fluid. Examples for such applications can be found in the medical, biotechnology or chemical field. Typical examples for the applications mentioned are the isolation of target substances from cell suspensions, e.g. proteins or peptides which have been produced by specifically modified cells, such as antibodies or hormones; the removal of target substances from blood or blood products, such as clotting factors; or the enzymatic modification or breakdown of substances in fluids, such as, for example, urea. Another important application is the extracorporeal removal of disease-causing substances from blood or blood components such as blood plasma during the treatment of a patient in need.

The treatment of the fluids is often performed by bringing the fluid into contact with a particulate material, wherein the material as such has a certain activity, e.g. for adsorbing a target substance, or wherein the material serves as a matrix for immobilizing functional groups which will selectively bind the target substance or which have a certain enzymatic activity. Accordingly, the interaction between the particulate material and the target substance may be based on the specific affinity between the carrier material and the target substance, wherein typically ligands with a specific affinity for the target substance in the fluid are coupled to the carrier material. Such ligands may specifically bind to one single target substance or, alternatively, to a group of targets having a certain common characteristic. Typically, such ligand may be an antibody against a target substance. Alternatively, the ligand may be a substance which an antibody will specifically bind to. Ligands may also consist of charged groups which will then bind to the target substances having the respective opposite charge. The interaction may equally be based on hydrophilic or hydrophobic interaction, cationic or anionic exchange, adsorption, enzymatic or catalytic reactions or the like. The particulate material may also be used a source of substances which are released from the particulate material into the fluid that passes said material. In extracorporeal blood treatment applications, the release of heparin or thrombin may be mentioned as examples for such use.

Several medical applications of devices are known which combine, within the filter device, hollow fiber membranes which are arranged as a bundle within the device, and particulate material which is either distributed in the filtration space of the device, i.e. around the hollow fibers, or connected in series within a cartridge or directly within the same housing to the hollow fiber membrane module (see, for example, US 2002/0125184 A1). For a number of applications it is necessary or desirable to subject a fluid to be treated to different subsequent treatments. In case of bioprocessing applications, it may be necessary to first remove larger particles with a prefilter before subjecting the fluid to an affinity chromatography, or, especially with regard to medical applications, to keep certain components of the fluid separate from the affinity chromatography matrix. In all such applications, however, it is important to achieve high productivity and selectivity with regard to the treatment. The varying requirements of any such treatment can be met by adapting either the hollow fiber membranes and/or the particulate material used.

Several devices containing both hollow fiber membranes and particulate material on the outside of the hollow fibers have been described already in the prior art. However, the prior art does not provide for any teaching or description of the final design of such hollow fiber membrane module and no modules of this design have become publicly known or are actually in use, probably because of the many problems connected with the optimal construction of such device which has to allow sufficient permeation of flow so that target substances that enter the filtrate space of the device are distributed throughout the active particulate material.

EP 0 341 413 describes an adsorber module for the treatment of whole blood, wherein the blood flows through the lumen of the hollow fibers. Plasma enters the filtrate space as permeate. In one embodiment, the module described has no outlet for the plasma, which instead reenters the lumen of the hollow fibers. The module, however, does not comprise active particulate material in the filtrate space but the functional groups are immobilized on the pores and the outer shell of the membrane.

US 2003/0111414 A1 is directed to a membrane module for substance-specific treatment of fluids comprising two membrane elements, having a porous, semipermeable wall, each having one end pointing toward the distribution space and the other toward the collection space and a cavity formed by the wall, wherein the first membrane elements are embedded in a first sealing compound at the end pointing toward the distribution space and in a second sealing compound at the end pointing toward the collection space, such that the ends extend through the sealing compounds and each of the cavities of the first membrane elements is open at the end pointing toward the distribution space as well as at the end pointing toward the collection space and opens into the distribution space and collection space.

US 2011/0218512 A1 relates to antiviral therapy methods comprising passing blood or plasma through a lectin affinity hemodialysis device. In the device, blood is passed through the lumen of a hollow fiber membrane, wherein lectins are located in the extraluminal space of the cartridge, which accepts and immobilizes the viruses. The device is designed in a way to allow the in situ produced plasma to leave the device through a plasma outlet port. The plasma thus does not re-enter the lumen of the hollow fibers.

US 2009/0304677 A1 relates to methods for removing microvesicular particles such as exosomes from blood, wherein, in one specific embodiment, the blood is run through an extracorporeal circulation circuit that uses a hollow fiber cartridge. The membranes of said hollow fibers have sufficient permeability for the microvesicles to be removed through the membrane of the hollow fibers and into an area outside of the fibers containing agents capable of adhering to the microvesicles in a manner such that said microvesicles are attached to said agent and do not substantially re-enter the hollow fibers. However, the preparation and/or use of such device have not been described and have not publicly become known.

In modules which do not have an outlet for the fluid which enters the filtrate space either directly or by passing through the hollow fiber membrane wall, the fluid or permeate has to enter or re-enter the hollow fiber lumen for being removed from the module. In such situations, the flow tends to be higher in the inlet region and lower in the lower part or outlet region of the module. If the packing of the particulate material is not homogenous, this problem becomes even more pronounced and the adsorptive, binding or enzymatic activity of the particulate material in the inlet region is soon exhausted, whereas other regions are hardly used. In addition, fluid flows through particulate material of varying particle sizes and diameters at various rates and pressures. Fluid flows at a higher rate and at a lower pressure through particles of larger diameter. Conversely, fluid flows at a slower rate and at a higher pressure through particles of smaller diameter. The flow of a fluid through a filter module where particulate material is present in the filtrate space of the device or where the module is completely filled with such particulate material takes different directional flow paths through the particulate material. For example, fluid flow through a material containing large diameter particles disposed in a filter module is essentially laminar. However, larger particles may have the drawback of reduced active surface area and at a certain size may no longer be positioned in a filter module comprising a hollow fiber bundle without disrupting the homogenous distribution of the fibers within the module. On the other hand, fluid flow through a material containing small diameter particles with a high active surface area is no longer laminar. In general, the fluid flows in the direction of areas of least pressure which tend to be areas between the inner wall of the tubular housing and the particulate material and/or in areas of less dense packing of the particles, resulting in the fluid bypassing the majority of the surface area of the functional particulate material. As a result, the treatment of the fluid in question especially with filter modules comprising a hollow fiber membrane bundle and particulate material surrounding the fibers is inefficient.

A need therefore exists for a hollow fiber membrane module having an active particulate material on the filtrate side of the module assembly that improves the filtering efficiency of a fluid by providing a device with an optimized choice and allocation of the hollow fiber membranes in the module and an optimized choice and especially distribution of particulate material in the filtrate space between and around the fibers. The optimized device must allow sufficient permeation of flow so that target substances that enter the filtrate space of the device are distributed throughout the active particulate material.

SUMMARY

It is an object of the present invention to provide improved hollow fiber membrane modules comprising chemically and/or physically active particulate material in the filtrate space of the module for the treatment of fluids in bioprocessing or medical applications, wherein the module (1) comprises a cylindrical filter housing (2), a bundle of essentially parallel hollow fibers (3) distributed longitudinally within said housing (2), wherein the open ends are in fluid communication with a distribution space (6a) and with a collection space (6b), and wherein the ends are embedded in a sealing compound (5) such that the open ends of the hollow fibers (3) extend through the sealing compound (5), a filtrate space (4), which is closed off from the distribution space (6a) and the collection space (6b) and the lumen space of the hollow fiber membranes (3) and which is optionally interconnected with an inlet means (7a) and/or an outlet means (9), an inlet means (7a) for feeding the fluid into the filtrate space (4) or an inlet means (7b) for feeding the fluid into the distribution space (7b) which is fluid communication with the lumen side of the hollow fiber membranes (3), a first outlet means (8) for removing the treated fluid from the housing (2), said first outlet means being in fluid communication with collection space (6b), and optionally a second outlet means (9) for removing treated fluid from the filtrate space (4), characterized in that the filtrate space is homogenously populated with a particulate material being capable of interacting with at least one component of the fluid with a filling ratio of between 0.6 and 1.0. The modules are designed to provide an optimized permeation of flow so that target substances present in a fluid that enter the filtrate space of the device are distributed throughout the active particulate material and will be immobilized, removed, released or converted with a very high efficiency. In a further embodiment of the invention, the filling ration of the module according to the invention is between 0.7 and 1.0. In yet another embodiment of the invention, the filling ratio of the module according to the invention is between 0.75 and 0.95.

One embodiment provides for a hollow fiber allocation within the module of between 15% and 70%. In one embodiment of the invention, the hollow fibers used are plasma separation membranes. In another embodiment of the invention, the hollow fibers used are doped membranes having particles integrated into the membrane wall of the hollow fibers. In yet another embodiment of the invention, the hollow fibers consist of a high cutoff membrane which allows passage of larger molecular weight substances of up to about 70 kD. In still another embodiment, the hollow fibers used can be membranes which are generally used in given applications.

Another embodiment provides for particulate material that consists of particles having a diameter of between 1 μm to 400 μm.

The particulate material comprises carrier material which may be used as such or which is additionally functionalized by covalently or non-covalently attaching thereto reactive species, be it a substrate, a reagent, a catalyst or a scavenger.

In another embodiment of the invention, the particulate material, i.e. the particles it consists of, is homogenously or evenly distributed within the filtrate space. This means that the average number of particles per given volume, such as, for example, a square cm', is essentially the same within at least the lower two thirds of the internal space of the module.

One embodiment of the invention relates to the method of preparing hollow fiber membrane modules having the characteristics set forth above. In one embodiment of the invention, the particulate material is filled into the filtrate space in its dry state, wherein the filter module is held in an inclined position. In another embodiment of the invention, the particulate material is filled into the filtrate space as a suspension. In one embodiment, the dry particulate material or the suspension of the material may be introduced into the filtrate space from top to bottom through inlet port (7a). In another embodiment of the invention, the suspension may be introduced into the filtrate space from bottom to top through outlet port (9), wherein the filter module is held in a vertical position. In the context of the present invention, the expression "inlet port" or "outlet port" are assigned to certain ports, irrespective of their actual use. For example, an "outlet port" like outlet port (9) may be used to remove fluid from the device and thus serve as a genuine "outlet", but may also be used to introduce fluid into the device, thus serving as an "inlet". However, in order to avoid double assignments, the respective ports have been named either "inlet" or "outlet" ports without restricting the ports to a certain use.

In one embodiment, the filling process is accomplished with a filling device (10) which is designed to allow positioning the module (1) at any angle of inclination, preferably between 45° and 90° C. in regard to its longitudinal axis. In one embodiment, the module is mounted in a vertical position, i.e. at an angle of 90° C. (FIG. 3b). In one embodiment, the process comprises alternately rotating the module clockwise and counter-clockwise around its longitudinal axis in quick succession with a minimum total angular displacement (θ) of about 10° (see FIG. 4). The rotational movement of the module during filling the filtrate space, optionally in combination with a certain angle of inclination, allows for an improved distribution and deposition of the particulate material between the hollow fibers over the complete utilizable space of the housing.

In yet another embodiment, the module during the process of filling is additionally exposed to a force which is applied perpendicular to the longitudinal axis of the module with the help of a rapping means. Such pushing or rapping impact on the filter module during filling further improves the homogenous distribution and deposition of the particulate material in the filtrate space. It further increases the amount of particulate material which can be homogenously deposited in the filtrate space of the module.

In one embodiment of the invention, the filter module is used in affinity chromatography or separation applications comprising, without limitation, bioprocessing applications, such as the cleaning of monoclonal antibodies, removal of proteases, DNases or RNases for stabilizing biological fluids or recovering target substances such as peptides or enzymes from cellular products downstream of cell fermentation, or for the production and separation of substances in pharmaceutical production processes. In general, the expression "affinity chromatography" refers to a method of separating biochemical or biological mixtures based on a highly specific interaction such as that between antigen and antibody, enzyme and substrate, or receptor and ligand.

In another embodiment of the invention, the filter module is used in affinity chromatography or separation applications in extracorporeal treatments, comprising the treatment of whole blood, blood plasma or other blood products, for example for recovering or therapeutically removing blood components from the blood or the blood products.

BRIEF DESCRIPTION OF THE DRAWINGS

FIG. 7 shows CT scans of cross-sections through hollow fiber filter modules, wherein HI modified beads are made visible. The hollow fibers can be seen as dark dots which are more or less evenly distributed over the cross-section. White portions represent beads. Darker (black) areas represent regions without beads where no X-rays are being absorbed.

FIG. 8 shows the longitudinal sections of the filter modules which were prepared according to Example 4 and as used for the cross-sections of FIG. 3. Evenly distributed grey lines represent the hollow fibers within the module.

FIG. 11A through 11D shows the CT scans of a module which has been filled with a suspension of particulate material according to the invention and with a filling ratio of 0.85. FIG. 11B is a cross-section through the upper third of the filter, FIG. 11C through the middle section and FIG. 11D through the lower third of the filter. There are essentially no dark sections visible which represent voids where no particulate material is located.

FIG. 12A through 12D shows the CT scans of a module which has been filled with a suspension of particulate material according to the invention and with a filling ratio of 0.85. FIG. 12B is a cross-section through the upper third of the filter, FIG. 12C through the middle section and FIG. 12D through the lower third of the filter. There are essentially no dark sections visible which represent voids where no particulate material is located.

DETAILED DESCRIPTION

Figure 1:
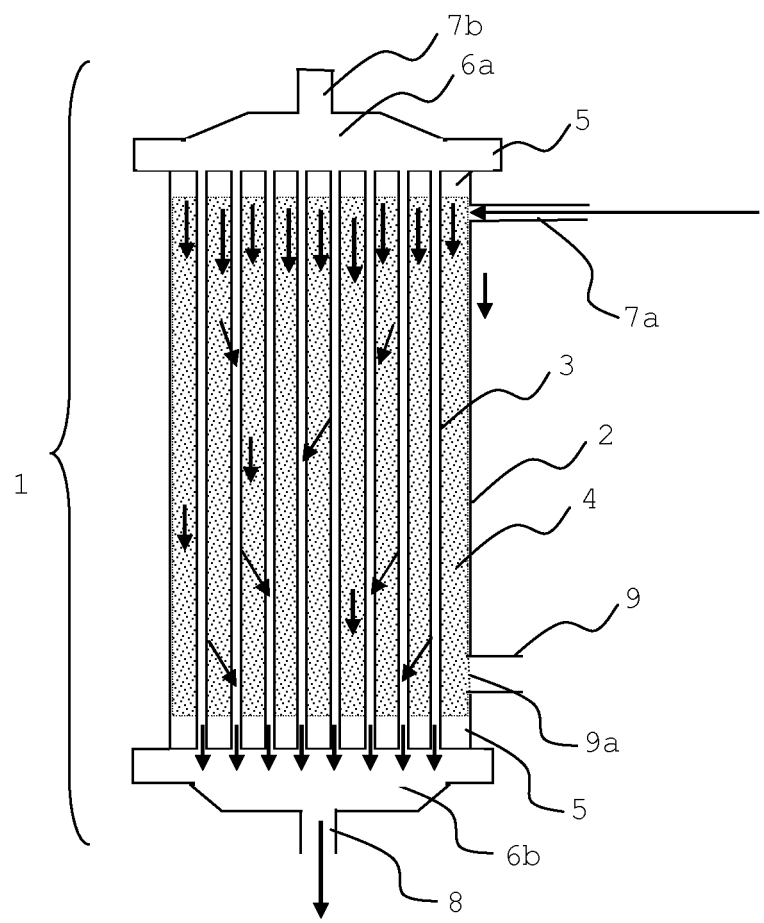
FIG. 1 shows a schematic representation of a hollow fiber membrane module according to the invention. The module comprises a plurality of hollow fibers (3) within a housing (2), a distribution space (6a) and a collection space (6b), as well as sealing compounds (5). The filtrate space (4) is filled with particulate material. The fluid to be treated enters the module (1) at inlet port (7a) and flows through the particulate material in order to be treated. The fluid, or such portions which are capable thereof, eventually passes the hollow fiber membrane walls and enters the lumen space of the fibers from where it finally leaves the device through collection space (6b) and outlet port (8). The fluid may re-enter and again leave the filtrate space during the process. Inlet port (7b) is not used in this case. Outlet port (9) may be used as a second exit site for the treated fluid and a negative pressure may be applied to enforce the process. In such case, a retention means (9a) needs to be in place which withholds the particulate material in the filtrate space.
Figure 2:
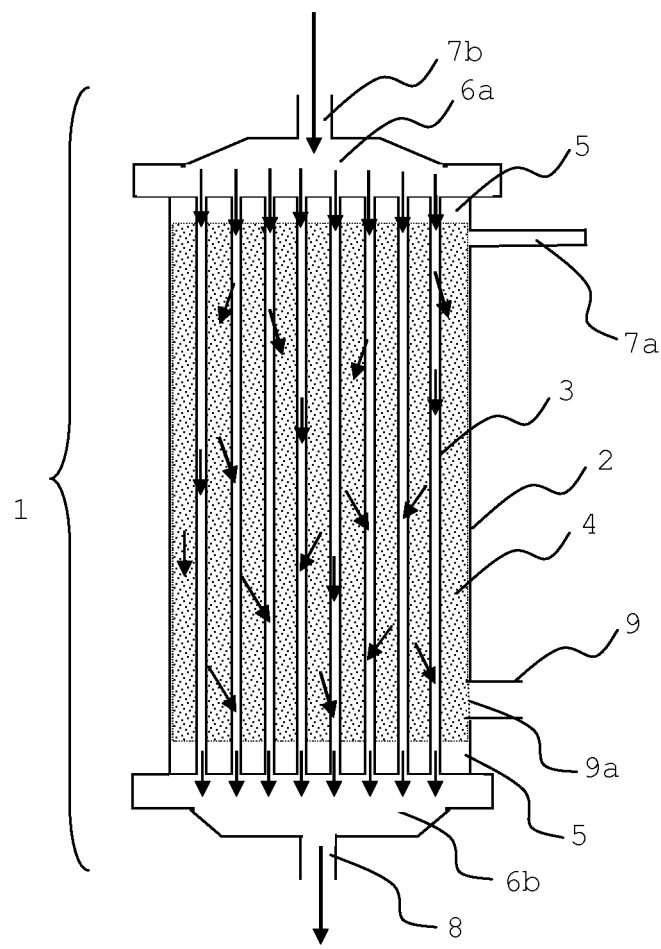
FIG. 2 again shows a schematic representation of a hollow fiber membrane module according to the invention and as shown in FIG. 1. In this case, the fluid to be treated does not enter the module at inlet port (7a) but is introduced via inlet port (7b) from where it enters the distribution space (6a) and finally the lumen of the hollow fibers (3). The fluid or such portions as may pass the hollow fiber membrane wall enters the filtrate space (4) and contacts the particulate material distributed therein. The treated fluid leaves the module by again passing the membrane wall, entering the lumen of the hollow fibers and leaving the module at outlet port (8) as described before for FIG. 1.

It is an object of the present invention to provide improved hollow fiber membrane modules comprising chemically and/or physically active particulate material in the filtrate space of the module for the treatment of fluids in bioprocessing or medical applications.

The expression "target substance" as used herein means substances or compounds which are distributed in a fluid and which are either to be recovered from said fluid for reasons of purification and further use or which are to be removed from said fluid to be discarded.

The expression "particulate material" as used herein refers to the material which is filled into and populates the filtrate space of a hollow fiber membrane module or filter. The particulate material is generally referred to, throughout the description, as consisting of particles having a certain average diameter. Said particles, for the sake of simplicity, are deemed to have a convex shape, the diameter of which is defined to be the largest distance that can be formed between two opposite parallel lines tangent to its boundary, and the width is defined to be the smallest such distance. In general the particles are assumed to be essentially spherical in nature, meaning that diameter and width are the same.

The expression "homogenous" as used herein means that the particulate material, i.e. the particles it consists of, is evenly distributed over the filtrate space (see, for example, FIG. 11B-11D). This means that the average number of particles per volume, for example $cm^3$, is essentially the same over the complete volume space of the dialyzer. The expression "essentially the same" used in connection with the average number of particles in a $cm^3$ means that the number of particles in a given volume area of 1 $cm^3$ may differ from the number of particles in a second volume area of 1 $cm^3$ only by up to 20%. Such homogenous distribution is mandatory, according to the invention, at least in the lower three quarters of the module, but should be homogenous preferably over the complete length of the device.

The expression "carrier material" as used herein may be equivalent to the expression "particulate material" or may refer to a material which is further functionalized before it is used as a "particulate material" and filled into the filtrate space of a device according to the invention. It is clear from the respective context which meaning has to be attributed to the expression. Accordingly, in one embodiment of the invention, the carrier material is directly used for being filled into the filtrate space of the device according to the invention. In another embodiment of the invention, the expression "carrier material" refers to a basic matrix which is further functionalized by covalently or non-covalently attaching thereto reactive species, be it a substrate, a reagent, a catalyst or a scavenger, before it is used within a device according to the invention. Reactive species or functional groups comprise, for example, substances having affinity to a target substance, such as ligands for affinity separation which may act selectively or non-selectively, and which can be attached to the carrier material directly or via spacers. Methods for attaching ligands to a surface are known in the art. Functional groups which may be attached to the carrier material can also be substances having enzymatic activity, such as enzymes. Functional groups may otherwise have ionic, hydrophilic or hydrophobic properties. In another embodiment of the invention and as mentioned before, "carrier material" as such already exhibits chemical or physical activity, such as, for example, ionic, hydrophobic or hydrophilic properties, which can be used for binding to or adsorbing one or more target substances or certain target substance classes from the fluid to be treated in accordance with the invention. The terms "carrier material" and "particulate material" may thus be used interchangeably. The particulate material, in the context of the present invention, may thus be carrier material which already has a functionality or which is further modified with specific chemical groups or ligands for certain applications.

The expression "adsorption" as it is used herein refers to the preferential partitioning of substances from liquid phase onto the surface of a solid substrate (the particulate material). Physical adsorption is caused mainly by van der Waals forces and electrostatic forces between adsorbate molecules and the atoms which compose the adsorbent surface. Thus adsorbents are characterized first by surface properties such as surface area and polarity. Non-polar adsorbents are generally referred to a as "hydrophobic". Carbonaceous adsorbents, polymer adsorbents and silicalite are typical non-polar adsorbents.

In one embodiment of the invention, the particulate material present in a module according to invention consists of particles having an average diameter of from 1 μm to 400 μm. The size of the particles influences the properties of a module according to the invention, as the particle size together with the porosity of the material has an impact on the capacity and performance of the particles. On the one hand, it is possible to enhance the adsorptive capacity of the particulate material by using smaller particles of a given species and/or by grinding particles. On the other hand, using very small particles, especially particles below an average diameter of about 100 μm, often results in an increased flow resistance which leads to a reduced exchange of substances. If the particles become too small, the exchange of substances may even come to a standstill. With particles having an average diameter of between 1 μm and 400 μm it is generally still possible to control and optimize the exchange of substances in a device according to the invention. For example, it is possible to respond to an increased flow resistance due to the use of small particles with an increase in packing density (fiber allocation). With particles having a larger average diameter, it is possible to use a lower packing density. However, it is advisable to use higher packing densities if the homogeneity of the distribution of the particulate material needs to be improved. With particles having a larger diameter, it may become difficult to evenly distribute such particles between the hollow fibers, again resulting in voids which should expressly be avoided. In addition, larger particles are more prone to damage the hollow fibers.

Carrier materials or particulate materials which can be used according to the present invention as set forth above are widely known in the art and are often commercially available. Carrier materials can be, without limitation, selected from the group comprising silica gel, dextran, agarose, nylon polymers, polymers of acrylic acid, methacrylic acid, co-polymers of ethylene and maleic acid anhydride, aminopropylsilica, amino-celite, glass beads, silicate containing diatomaceous earth or other substrates or matrices known in the art.

According to one aspect of the present invention, the particulate material may consist of uncharged, hydrophobic particles, comprising carbonaceous adsorbents, polymer adsorbents and hydrophobic silica, such as, for example, styrenic polymers like DOWEX™ OPTIPORE™ L493 and V493 or Amberlite® XAD®-2, polydivinylbenzene polymers or styrene-divinylbenzene copolymers (e.g. Amberlite® XAD4), poly(l-phenylethene-1,2-diyl) (Thermocole), activated carbon or hydrophobic silica, which is silica that has hydrophobic groups chemically bonded to the surface, or combinations thereof. Hydrophobic silica can be made both from fumed and precipitated silica. Hydrophobic groups that can be used are, for example, alkyl or polydimethylsiloxane chains. Carbon particles which may be used according to the invention can be derived, for example, from carbon such as Printex® XE2 (Degussa AG).

According to another aspect of the present invention, the particulate material may consist of cation exchange particles which may be used without further modification. Such cation exchange material is generally based on matrices of agarose, cellulose, dextran, methacrylate, polystyrene or polyacrylic acid. Such materials are generally known and often commercially available, for example, under trade names such as Sepharose® CM, CM, Sephadex, Toyopearl®, Amberlite®, Diaion™, Purolite®, Dowex® and Duolite® SO$_3$H, respectively.

According to another aspect of the present invention, the particulate material may consist of anion exchange material which can be used without further modification. Such anion exchange material may be based on polystyrene or styrene-divinylbenzene and which may be unmodified or modified with sulphonic acids, polyamines or quaternary or tertiary amines. According to one aspect of the invention, the particles are based on a copolymer of styrene and divinylbenzene carrying active groups such as quaternary ammonium groups, dimethylethanolamine groups, dimethylethanolbenzyl ammonium groups, benzyltrialkyl ammonium groups, benzyldimethyl(2-hydroxyethyl) ammonium and/or trimethylbenzyl ammonium functional groups. According to a specific aspect of the present invention, the particles used are based on a copolymer of styrene and divinylbenzene carrying quaternary ammonium groups. According to one aspect of the invention, the copolymer of styrene and divinylbenzene carries trimethylbenzyl ammonium functional groups, which is also referred to as Cholestyramine, Cuemid, MK-135, Cholbar, Cholbar, Questran, Quantalan, Colestyramine or Dowex® 1x2-Cl. Such anion exchange media which can be used are known, for example, under the trade name Amberlite®. Amberlite® comprises, for example, a matrix formed of styrene-divinylbenzene having active or functional groups such as quaternary ammonium groups, bezyldimethyl (2-hydroxyethyl) ammonium groups or dimethylethanolamine groups. Other anion exchange media which can be used are known for example, under the trade name Dowex®. Dowex® comprises, for example, a matrix formed of styrene-divinylbenzene which may have active or functional groups such as trimethylbenzylammonium.

According to yet another aspect of the invention, the particulate material is chosen from a group of materials comprising anion exchangers, cation exchangers, hydrophilic adsorbents, hydrophobic adsorbents, immunoadsorbents, adsorbents comprising affinity ligands attached thereto and mixtures thereof.

According to still another embodiment of the invention, the particulate material is chosen from polymeric adsorbents, such as, for example, nylon polymers, polymers of acrylic acid, methacrylic acid, co-polymers of ethylene and maleic acid anhydride, styrenic polymers, polydivinylbenzene polymers, styrenedivinylbenzene copolymers, or mixtures thereof.

In one embodiment of the invention, the carrier material is used in the form of beads, which are small, essentially spherical particles which may differ in size and composition and can have an average diameter in the range of from 100 nm to 5 mm and especially in the range of from 10 µm to 500 µm. Beads comprise, for example, rigid, porous particles, such as, for example silica beads, with a controlled pore size, wherein the pore size distribution can vary over a wide range and can be chosen according to the specific needs; magnetic beads, such as magnetic polysaccharide-polystyrene, silica-polystyrene, silicapolysaccharide, polysaccharide-poly(alkylcyanoacrylate) or polysaccharide-poly(lactic acid) particles; particles based on hydrophilic polymer gels, such as, for example, dextrans, poly(N-isopropyl acrylamide), poly(vinylmethylether) or poly(2-hydroxyethylmethacrylate).

Suitable beads are, for example, commercially available resins known to a person with skill in the art. In one embodiment of the invention, Tosoh Toyopearl® AF Amino or Epoxy 650-M can be used. Toyopearl® is a methacrylic polymer incorporating high mechanical and chemical stability. Toyopearl® AF-Epoxy 650-M is an activated support resin for affinity chromatography and has an epoxide functionalization of 800 µmol/g. The product is prepared by a high density epoxy functionalization of Toyopearl® HW-65. This material is especially useful when low molecular weight species are to be coupled to the matrix. The particle size distribution is between 40 and 90 µm. Another suitable matrix is Toyopearl® AF-Amino 650-M which is a reactive support resin for affinity chromatography and has 100 µmol/mL amino functions. The product is prepared by introducing amino groups onto Toyopearl® HW-65. Aminoactivated material is able to immobilize ligands with carboxyl or formyl groups. Another commercially available matrix is Toyopearl® AF-Carboxy 650 M having 100 µmol/mL carboxylic functions.

Another commercially available matrix material is ChiralVision Immobead™ 350 or ChiralVision Immobead™ 150. This type of beads is a crosslinked copolymer of methacrylate carrying 100 µmol/g oxirane groups that is suitable for the covalent immobilization of a variety of enzymes. The porous beads are especially designed to have a low diffusion limitation that allows for the immobilization of enzymes with high specific activities. The particle size distribution is between 300 and 700 µm. A further commercially available matrix material is Mitsubishi ReliZyme™ EXE 135. The matrix is a crosslinked copolymer of methacrylate containing 166 µmol/g oxirane groups. The median pore diameter is between 40 and 60 nm, while the particle size range is 100-300 µm and 200-500 µm, depending on the product. Mitsubishi ReliZyme™ EXE 148 is an equivalent type of matrix, however with a smaller particle size (on average about 60 µm).

In one embodiment of the invention, the carrier material is modified by attaching thereto, with methods known in the art, reactive species. Such reactive species can be a substrate, a reagent, a catalyst or a scavenger. Such reactive species or functional groups comprise, for example, substances having affinity to a target substance, such as ligands for affinity separation which may act selectively or non-selectively, and which can be attached to the carrier material directly or via spacers. Ligands in the field of affinity chromatography are generally known in the art.

In one embodiment of the invention, such affinity separation relates to bioprocessing applications, comprising, without limitation, the cleaning of monoclonal antibodies, removal of proteases, DNases or RNases for stabilizing biological fluids, recovering target substances such as peptides or enzymes from cellular products downstream of cell fermentation.

In another embodiment of the invention, such affinity separation relates to the treatment of whole blood, blood plasma or other blood products, for example for recovering or therapeutically removing blood components from the blood or the blood products. The expression "blood product(s)" in the context of the present invention refers to any component of the blood which is collected from a donor. Most blood products consist of specific processed components such as red blood cells, blood plasma, or platelets. Examples include cryoprecipitate, PF24, fresh frozen plasma and cryosupernatant. Many blood products are made from the plasma component of blood. Plasma contains a large number of proteins, each of which performs a different role within the blood and be used separately as a blood product.

In one embodiment of the invention, a hemodialyzer or hemodiafilter can be connected in series with, or directly coupled to, a filter module according to the invention. The hemodialyzers or hemodiafilter will then remove the substances which are normally cleared by such hemodialyzer or hemodiafilter. In the subsequent filter module according to the invention, in which whole blood passes the filter module through appropriately chosen hollow fiber membranes, such as, for example, plasma separation membranes, toxins can be removed from the blood by providing the appropriate functional group on the particulate material in the filtrate space, which otherwise cannot be removed by standard hemodialysis or haemodiafiltration methods. The expression "toxins", in the context of the present invention, means substances which negatively influence the health of a person, including exogenous substances which have been taken up by such person or endogenous substances which have been generated within the body, such as, for example, cytokines, and pyrogens.

In another embodiment of the invention, the filter module of the invention receives the dialysate of the hemofilters or hemodiafilter, which contains the substances which have been cleared from the blood of a patient. Depending on the nature of the membrane used in such hemofilter or hemodiafilter, the dialysate contains the substances normally eliminated by standard hemodialysis or hemodiafiltration methods, such as, for example, urea, or larger molecules of up to 30 kD or of up to 40 kD or of up to 50 kD or of up to 60 kD or of up to 70 kD or of up to 80 kD. Like that, membranes having pores with a larger size may allow the passage of, for example, cytokines, albumin and albumin-bound toxins. The filter module according to invention may be adapted with an appropriate particulate material with regard to one or more specific target molecules which have to be eliminated from the dialysate, for example in order to clean or recycle the dialysate for further use. In such cases the particulate material may comprise immobilised urease and/or sorbent particles for the removal of waste from used dialysis fluid, comprising activated carbon or charcoal which is known to remove heavy metals, oxidants, and waste products, and/or acid ion exchange material for absorbing ammonium ions which may be produced by the urease, such as described, for example, in US 2010/004588 A1.

In yet another embodiment of the invention, the filter module according to the invention directly receives body fluids for removing body wastes or toxic substances from the fluid, such as, for example, whole blood, plasma or peritoneal fluid. The module thus functions immediately by removing wastes from the body fluid. In the case of whole blood, the use of plasma separation hollow fiber membranes allows the direct clearance of toxins from the in situ produced plasma which interacts with the particulate material in the filtrate space before it re-enters the hollow fiber lumen where it reunites with the main flow path and the cellular blood components and leaves the module at the outlet port to be returned to the patient. The clearance rate of toxins in such embodiment depends on the plasma flow rate through the particulate material, the binding rate of the particulate material and the residence time in the particulate material of the module. If the binding rate of a given particulate material is relatively slow, then the flow rates should be adapted in a way that the residence time of the fluid to be treated is sufficient to allow for the effective clearance of the target substance. Accordingly, for a given target molecule and particulate material, the best range of plasma flow rates can be determined which optimizes the target substance clearance rates.

Functional groups which may be attached to the carrier material can also be substances having enzymatic activity, such as enzymes. The enzyme coupled to the spacer can be chosen among the known classes of enzymes. Enzymes of interest may be, for example, oxidoreductases, transferases, hydrolases, lyases, isomerases or ligases. As specific enzymes, ureases or esterases could be mentioned. In one embodiment, only one type of enzyme is immobilized on the support. In another embodiment, a mixture of two or more enzymes is immobilized. Such systems can be of interest if a product of a transformation by a first enzyme becomes a substrate for a second enzyme. Examples for such immobilized enzymes can be found, for example, in EP 2 316 932 A1, included herein by reference. Functional groups may otherwise have ionic, hydrophilic or hydrophobic properties. Functional groups which can be attached to the carrier material, for example for providing ionic groups, are shown in EP 1 518 870 A1, the content of which is expressly included herein by reference.

According to the present invention it is possible to combine various particulate materials in one filter module according to the invention. For example, it is possible to combine particulate materials having different functionality or having different functional groups immobilized thereon. It is advisable, however, to combine particulate material which has essentially the same density in order to achieve a homogenous distribution of the admixed particles within the filtrate space according to the invention. If the density of the particulate materials used differs by more than 20%, it is difficult to homogenously introduce and distribute the particulate material within the filtrate space of the housing.

As mentioned before, the particulate material present in a module according to invention consists of particles having an average diameter of from 1 μm to 400 μm. In another embodiment of the invention, the particles have an average diameter of from 1 μm to 100 μm. In yet another embodiment, the particles have an average diameter of from 100 μm to 200 μm. In yet another embodiment, the particles have an average diameter of from 200 μm to 300 μm. In yet another embodiment, the particles have an average diameter of from 300 μm to 400 μm. In yet another embodiment, the particles have an average diameter of from 100 μm to 400 μm. A number of materials which can be used as particulate or carrier materials are subject to swelling, i.e. they will increase in average diameter upon contact with water or an aqueous solution. For example, most ion exchange materials are provided as gels. Such ion exchange resins are hygroscopic, and the amount of moisture hydrated by the material depends on the cross-linking and the type of functional group. Low crosslinking gel resins with functional groups such as quaternary ammonium contain large amounts of water. The addition and removal of water thus results in swelling and contraction. In the context of the present invention, the average diameters given relate to the maximum average diameters of the materials, i.e. after swelling.

The expression "filling ratio" as used herein, refers to the ratio of the volume in ml of the maximal amount of particulate material, in its dry form or wet form, respectively, which can be accommodated in the filtrate space of a given hollow fiber membrane module ($V_{PM}$) and the utilizable volume in ml of the filtrate space of said module ($V_{FS}$):

$$\text{Filling ratio} = \frac{V_{PM}(\text{ml})}{V_{FS}(\text{ml})}.$$

$V_{PM}(\text{ml})_{PM}$ thus represents the volume of the particulate material which could be accommodated in the filtrate space of the device. $V_{FS}(\text{ml})$ represents the utilizable filtrate space, which is known or can easily be determined for a given hollow fiber membrane filter module.

A ratio of 1.0 would thus mean that the complete utilizable volume of the filtrate space is occupied by the particulate material. The lower the ratio gets, the less particulate material is present in the filtrate space of the module. The filling ratio always refers to modules wherein essentially the complete utilizable volume of the module has been exhausted. "Exhausted", in the context of the present invention, means that no more particulate material can be filled into the device. $V_{PM}(\text{ml})$ can be calculated from the total amount of particulate material in g which can been filled into the module with a given method, divided by the bulk density (g/ml) of the material. The bulk density of a particulate material is defined as the mass of the particles of the material per total volume they occupy. It should be noted that the bulk density of a particulate material can change depending on how the material is treated. For example, the particulate material, simply poured into a cylinder, will have a certain bulk density ("bulk density"). If the cylinder is agitated, the particles will move and usually settle closer together, resulting in a higher bulk density. For this reason, the bulk density of the particulate material in a module which was prepared according to the invention is referred to as a "tapped density" (ρ), which in principle refers to the bulk density of the particulate material after compaction. For a given material ρ can be determined according to DIN ISO 3953. The maximal bulk density ("tapped density") is reached when no further compaction of the material takes place.

The volume $V_{PM}$(ml) of the particulate material which can be accommodated in the filtrate space of a given hollow fiber membrane module can thus be calculated:

$$V_{PM}(\text{ml}) = \frac{m_{PM}(\text{g})}{\rho(\text{g/ml})}.$$

$m_{PM}$ represents the amount of particulate material which could be accommodated in the filtrate space of the module. $m_{PM}$ can be determined for example by subtracting the amount of remaining particulate material (filtered off and dried, in case the material was filled into the module as a suspension) from the initial quantity of (dry) particulate material (see Example 1). $\rho$ represents the tapping density of the particulate material in g/ml according to DIN ISO 3953.

The fiber allocation or packing density in the cylindrical filter housing can be between 15% and 75%. In the context of the present invention, the fiber allocation is calculated from the percentage of the cross section surface allocated by the fibers per utilizable cross section surface in the filter housing. The utilizable cross section surface corresponds to the cross section surface. The theoretical maximum packing density would thus correspond to an allocation of 100%. In reality, packing densities of up to 70% or 75% can be reached, depending on the fibers used.

Accordingly, in one embodiment of the invention, the fiber packing density or fiber allocation is in the range of 15% to 75%. The fibers preferably are homogenously distributed over the length of the cylindrical housing of the filter module, which means that the distance between the single fibers remains essentially the same over the total length of the fibers. In another embodiment of the invention, the fiber allocation is between 20 and 55%. In yet another embodiment of the invention, the fiber allocation is between 45% and 70%. In still another embodiment, the fiber allocation is between 20% and 45%.

The fibers which can be used for producing a module according to the invention can be straight or crimped, wherein crimped fibers are fibers having a certain ondulation which is essentially sinusoidal but may deviate from such sinusoidal ondulation over the length of the fiber, i.e. wavelength and/or amplitude of the crimps of one fiber or of two or more fibers may be different. Ondulated fibers and methods for ondulating fibers are known in the art and have been described, for example, in EP 1 257 333 A1. It is possible to combine straight and crimped fibers in one device. In one embodiment of the invention, all of the fibers in the filter module are ondulated. In another embodiment of the invention, all of the fibers in the filter module are straight fibers.

The kind of hollow fibers used in a module according to the invention may vary over a broad range depending on the specific application the module is prepared for. In one embodiment of the invention, the pores of the hollow fiber membranes have to allow passage of the target substance from the fluid which flows through the lumen of the hollow fibers into the filtrate space where it may interact with the chemically and/or physically active particulate material which populates the filtrate space. In another embodiment of the invention, the pores have to allow the passage of the treated fluid from the filtrate space into the lumen of the hollow fibers and out of the filter module. The respective target substance or substances will remain within the filtrate space or will also pass the hollow fiber membrane wall in altered form (e.g. after enzymatic conversion).

As the membrane types may vary considerably depending on the application or therapy the respective module can be put to, the pore sizes of the membranes used for producing the module may vary over a wide range, for example, from between 3 nm and 1000 nm in diameter. On the one hand, the pore size and thus the membrane can be chosen depending on the size of the substances which are supposed to pass the membrane or, alternatively, which shall be prevented from passing the membrane. On the other hand, the pore size of the hollow fiber membranes also needs to be sufficiently small in order to prevent the particulate material on the filtrate side to pass the membrane wall and eventually enter the lumen of the hollow fibers. Average pore size diameters of membranes are generally known in the art as are the average diameters of the particles constituting the particulate material which is to be used. Thus, the correct membrane can be chosen accordingly by the person with skill in the art.

In one embodiment, the pores allow the passage of essentially all components of the fluid which is to be treated from the lumen space of the hollow fibers into the filtrate space. In another embodiment, the pores allow the passage of only a portion of the fluid which has to be treated and retain larger components from passing the membrane and entering the filtrate space.

In yet another embodiment, the pores allow the passage of essentially all components of the fluid which is to be treated from the filtrate space into the lumen space of the hollow fibers. In still another embodiment, the pores allow the passage of only a portion of the fluid which has to be treated into the lumen space of the hollow fibers and retain larger components from passing the membrane and entering the lumen space.

Various types of known hollow fiber membranes can be used for preparing modules of the present invention, depending on which use the membrane is put to. Accordingly, a wide variety of materials can be used for the membranes. Depending on the application of the module of the invention, the membrane can be made from organic polymers or blends thereof, wherein the polymers can be hydrophilic and/or hydrophobic. The polymers can be selected from the group comprising cellulosic polymers, such as, for example, cellulose or modified cellulose such as cellulose esters, cellulose ethers, amine-modified cellulose or combinations of such cellulosic polymers, synthetic polymers such as, for example, polyacrylonitrile based polymers, polymers comprising polyurethanes, polysulfones or polyaryl(ether)sulfones such as polysulfone or polyethersulfone, polyvinylidene fluoride, polytetrafluoroethylene, water-insoluble polyvinyl alcohols, aliphatic and aromatic polyamides, polyimides, polyetherimides, polyesters, polycarbonates, polyolefins such as polyethylene, polypropylene, polyvinyl chloride, polyphenylene oxide, polybenzimidazoles, and polybenzimidazolones, as well blends and combinations of these polymers. Other polymers can be mixed as additives with these polymers or polymer blends, for example, polyethylene oxide, polyhydroxyether, polyethylene glycol, polyvinylpyrrolidone, polyvinyl alcohol, or polycaprolactone.

It is also possible to use doped membranes which are characterized by having entrapped therein small particles such as, for example, ion exchange particles or carbon particles in an amount of preferably 5-40 wt.-%. Doped membranes have been described, for example, in European Patent Application No. 11193795.9, expressly incorporated herein by reference. It is also possible to make use of membranes which have been subjected to a surface modification, for example for establishing certain properties of the membrane surface such as, for example, polysiloxanes, or in the form of certain functional groups, such as, for example, described in European Patent Application Nos. 10181793.0, 09013610.2, 11176769.5 and 11176770.3.

According to one aspect of the invention, the hollow fiber membranes used for preparing the modules of the present invention comprise plasma separation membranes. Membranes suitable for plasma separation are known in the art and have been described, for example, in EP 1 875 956 A1 or EP 1 875 957 A1, all incorporated herein by reference. A plasma separation membrane which may be effectively used for preparing a product according to the present invention is an asymmetric plasma separation membrane which exhibits high permeability for the whole spectrum of plasma proteins and lipoproteins, reflected by a high sieving coefficient of >0.90. In plasma separation it is desired to have the total plasma protein in the separated plasma fraction, whereas the larger corpuscular components of the blood, like blood cells and cell debris, are retained by the membrane. Further, such a plasma separation membrane should exhibit a high surface porosity and total porosity of the membrane to achieve high filtration performance. It should also be characterized by a hydrophilic, spontaneously wettable membrane structure, low fouling properties for long term stable filtration, and low protein adsorption. Such a plasma separation membrane preferably has smooth surfaces in contact with blood, thus avoiding or minimizing haemolysis during blood processing. The membrane should show constant sieving properties and filtration behavior over the whole treatment period. It should further exhibit high biocompatibility, low or no complement activation and low thrombogenicity. Further, the plasma separation membrane used preferably has an inner diameter in the range of 100 to 500 µm. Lower inner diameters are disadvantageous because they result in too high wall shear rates and increased pressure drop in the fiber. On the other hand, if the inner diameters are too high, this would result in too low shear rates which increase the risk of haemolysis at low transmembrane pressures. The plasma separation membrane which can advantageously be used for the present invention has a wall thickness in the range of between 20 to 150 µm. Lower wall thicknesses are disadvantageous due to reduced mechanical properties of the fiber during production and during its use in the plasma separation module itself. Higher wall thicknesses are disadvantageous because they require increased time intervals to perform the phase inversion process resulting in instable process conditions and an instable membrane. Further, the membrane should have a pore diameter on the selective separation layer in the range of 0.1 to 1 µm. Lower average pore diameters are disadvantageous due to incomplete passage of total plasma proteins through the porous structure. Membranes which can be used in a module according to the invention are also used, for example, in filters known as Plasmylane®. According to one embodiment of the invention, the membrane surface area within a device according to the invention is in the range of from 0.4 m² to 1.2 m². According to another embodiment of the invention, the membrane surface area within a device according to the invention is in the range of from 0.5 m² to 1.0 m².

In another embodiment of the invention, the hollow fiber membrane which may be used for preparing a module according to the invention is a standard membrane for haemodialysis, haemofiltration or haemodiafiltration applications. Such membranes are known in the art. Hollow fiber membranes which may serve as a matrix in the present invention are described, for example, in EP 2 113 298 A1, EP 2 281 625 A1 or EP 2 228 126 A1, all incorporated herein by reference. Membrane types which can be used in a module according to the invention are also used, for example in dialysis filters known as Polyflux® Revaclear, Polyflux®, Optiflux®, Polysulfone®, Helixone® or FX class dialysers.

In yet another embodiment of the invention, the hollow fiber membrane which may be used for preparing a fluid treatment module according to the invention is a so called "high cut-off membrane" which allows substances with a molecular weight of up to 45 kD to pass the membrane with a sieving coefficient measured in blood according to EN1283 of up to 1.0. Such membranes may further have a molecular weight cut-off in water, based on dextran sieving coefficients, of between 90 and 200 kD. In another embodiment of the present invention, the high cut-off dialysis membrane is characterized by an average pore size, on the selective layer, of between 8 and 12 nm as determined according to Aimar et al.: "A contribution to the translation of retention curves into pore size distributions for sieving membranes". *J. Membrane Sci.* 54 (1990)339-354, $\alpha=0.33$ $(MM)^{0.46}$, wherein $\alpha$ represents the radius (in Å) from which the pore diameter can be determined. MM represents the molecular weight or molar mass (in g/mol) of dextrans. Such membrane is known in the art and has been described, for example, in PCT/EP2012/060246 or in European Patent Application No. 09006809.9, incorporated herein by reference. Membrane types which can be used in a module according to the invention are also used, for example, in filters known as HCO 11000 or Theralite®.

In yet another embodiment, the hollow fiber membrane which may be used for preparing a fluid treatment module according to the invention is a doped membrane wherein 5-40 wt.-% of particles having an average particles size of between 0.1 and 15 µm are entrapped and wherein the membrane has a wall thickness of below 150 µm, such as described in European Patent Application No. 11193795.9, incorporated herein by reference. In one aspect, said membranes have entrapped therein basic anion exchange material, which may be based on polystyrene or styrenedivinylbenzene and which may be unmodified or modified with sulphonic acids, polyamines or quaternary or tertiary amines. The particles can based on a copolymer of styrene and divinylbenzene carrying active groups such as quaternary ammonium groups, dimethylethanolamine groups, dimethylethanolbenzyl ammonium groups, benzyltrialkyl ammonium groups, benzyldimethyl(2-hydroxyethyl) ammonium and/or trimethylbenzyl ammonium functional groups. According to a specific aspect of the present invention, the particles in the membranes of this type are based on a copolymer of styrene and divinylbenzene carrying quaternary ammonium groups. The copolymer of styrene and divinylbenzene preferably carries trimethylbenzyl ammonium functional groups and is also known as Cholestyramine, Cuemid, MK-135, Cholbar, Cholbar, Questran, Quantalan, Colestyramine or Dowex® 1x2-Cl. Anion exchange media which can be entrapped are known, for example, under the trade name Amberlite®. Amberlite® comprises, for example, a matrix formed of styrenedivinylbenzene having active or functional groups such as quaternary ammonium groups, bezyldimethyl (2-hydroxyethyl) ammonium groups or dimethylethanolamine groups. Other anion exchange media which can be used are known for example, under the trade name Dowex®. Dowex® comprises, for example, a matrix formed of styrene-divinylbenzene which may have active or functional groups such as trimethylbenzylammonium. The particles entrapped in the membrane as contemplated here can also be based on vinylimidazolium methochloride vinylpyrrolidone copolymers, known, for example, as Luviquat®. It is also possible to use uncharged, hydrophobic particles, comprising carbonaceous adsorbents, polymer adsorbents and hydrophobic silica, such as, for example, styrenic polymers like DOWEX™ OPTIPORE™ L493 and V493 or Amberlite® XAD®-2, polydivinylbenzene polymers or styrene-divinylbenzene copolymers (e.g. Amberlite® XAD4), poly(1-phenylethene-1,2-diyl) (Thermocole), carbon or hydrophobic silica, which is silica that has hydrophobic groups chemically bonded to the surface, or combinations thereof. Hydrophobic silica can be made both from fumed and precipitated silica. Hydrophobic groups that can be used are, for example, alkyl or polydimethylsiloxane chains. Carbon particles which may be used according to the invention can be derived, for example, from carbon such as Printex® XE2 (Degussa AG).

In still another embodiment of the invention, the hollow fiber membrane which may be used for preparing a fluid treatment module according to the invention is a so-called "protein separation membrane" or "plasma fractionation membrane". Such membrane is characterized by allowing the passage of ≥90% of molecules having a molecular weight of below 100 kD, while molecules having a molecular weight of >1000 kD will pass the membrane wall only to a very limited extend (≤10%). The membrane thus allows to separate plasma in fractions with mainly larger proteins/lipids and smaller proteins, such as, for example, albumin. Membranes of this type are known and also commercially available, for example the "Monet®" filter (Fresenius Medical CareDeutschland GmbH).

In one embodiment of the invention, any one of the aforementioned membranes is based on polysulfone or polyethersulfone and a blend thereof with low and/or high molecular weight polyvinylpyrrolidone. In one embodiment thereof, a polyvinylpyrrolidone may be used which consists of a low molecular weight component having a molecular weight of below 100 kDa and a high molecular weight component having a molecular weight of 100 kDa or more. It yet another embodiment, the membrane may further comprise low amounts of additives, such as, for example, polyamide.

In one embodiment of the invention, the fluid enters the device (1) with or without pressure at the proximal inlet port (7b) and enters the lumen of the hollow fibers membranes (3). All or a portion of the fluid will pass through the wall of the hollow fiber membranes (3) into the filtrate space (4) where it will interact with the active particulate material deposited there.

The reduced luminal pressure at the distal end of the hollow fibers allows the treated fluid to re-enter the lumen of the hollow fibers (3) and leave the device (1) at the distal outlet port (8). If, for example, the fluid to be treated is blood, whole blood can be withdrawn from a subject using a pump, and pumped into the inlet port (7b) of the device (1). As blood flows through the hollow fiber membranes (3), plasma filters through and into the filtrate space (4) by convective flow. Pressure at the proximal inlet (7b) of the device (1) can be used to force plasma through the pores of the membrane (3), allowing the plasma to interact with the active particulate material which is located in the filtrate space (4). Blood cells and certain other blood components are too large to pass through the pores and remain in the lumen of the hollow fibers. At the distal outlet port (8) of the device (1), reduced luminal pressure allows the treated plasma to return into the lumen and admix with the blood as it exits the device (1).

In another embodiment, the main flow pump can be located downstream of the outlet (8) of the device (1). As used herein, "main flow" refers to the flow or flow path through the device on the same side of the membrane as the inlet. In yet another embodiment, a negative pressure pump can be installed in fluid communication with outlet port (9) of the device (1), wherein the pump is configured to assist the flow of the fluid to be treated from the hollow fiber lumen through the membrane (3) and the particulate material on the filtrate side (4), thereby increasing the contact between the fluid and the particulate material and, as a consequence, the clearance rate of the module. In yet another embodiment of the invention, the negative pressure pump which is in fluid communication with outlet port (9) may be used to assist in removing at least a portion of the treated fluid directly from the filtrate space (4). For example, in the case of plasma, at least a portion of the treated plasma may be withdrawn through outlet port (9) and reintroduced into the bloodstream of the device (1) downstream of outlet port (8) where the blood leaves the device (1). The flow rate of the assist pump which is in fluid communication with the filtrate space (4) and the outlet port (9) can be varied over a certain range and is preferably configured to provide a plasma flow rate of approximately 25% of the main fluid flow rate into the device. The plasma flow rate may also be configured in a way to increase the target substance clearance rate by at least two times over that of a system relying only on the flow without any plasma assist pump. As used herein, the term "in fluid communication" with a pump signifies that the pump is located along or within the fluid path, and includes set-ups where no components of the pump contact the fluid, such as a peristaltic pump. A pump which is located along or within a fluid path may or may not be in actual contact with the fluid. The term "clearance rate" as used herein means the amount of fluid which can be treated per time.

According to another embodiment of the invention, the device (1) further comprises a retention means (9a) for preventing the particulate material to leave the filtrate space (4) via outlet port (9) together with the treated fluid. Such means may consist, for example, of an essentially inert mesh, a microporous flat sheet membrane or a non-woven material, wherein the material can be chosen from a broad variety of materials which are characterized by their chemical stability and physical stability with regard to the negative pressure to be applied at outlet port (9). The mesh of the material can be adapted to the size of the particulate material in the filtrate space and is chosen in order to prevent the smallest particles of the material from passing through the retention means (9a).

In another general embodiment of the present invention, the fluid which needs to be treated enters the device at the proximal inlet port (7a) which is connected with the filtrate space (4) of the device (1). Pressure can be used at the inlet port (7a) to force the fluid through the filtrate space (4), allowing the fluid to interact with the active particulate material which populates the filtrate space (4). Again, a retention means such as retention means (9a) may have to be in place at inlet port (7a) which withholds the particulate material in the filtrate space. The fluid enters the lumen of the hollow fiber membranes (3) and leaves the device (1) at the distal outlet port (8) which is in fluid communication with the collection space (6b).

The time of exposure of the fluid to be treated to the particulate material depends on the flow rate and the usable volume space ($V_{FS}$) of the filtrate space comprising the particulate material. For example, if the main flow rate of a module is 100 ml/min and the usable volume space of the device is 100 ml, then running the untreated fluid for 60 minutes would expose 6000 ml of the fluid to the particulate material for 1 minute. Accordingly, the main flow rates can be adapted over a certain range according to the respective use of the module. In general, the main flow rate may vary over a broad range in bioprocessing applications. Generally, the flow rate will mainly be determined by the specific application. For extracorporeal therapies, wherein blood or plasma is being treated, the blood flow rate into the device will be from between 80 ml/min of up to 600 ml/min. In one embodiment, the blood flow rate will be from between 200 ml/min to 500 ml/min. In another embodiment, the blood flow rate will be 500 ml/min or less. In yet another embodiment, the blood flow rate will be from between 300 ml/min to 500 ml/min.

The fluid volume or usable volume space ($V_{FS}$) of the filter modules of the invention can also vary depending on the specific use the module is put to. In bioprocessing applications, the volume can vary over a very wide range. In one embodiment, the capacity of a module is from 5 ml to 5000 ml. In another embodiment, the usable volume space ($V_{FS}$) of the module is from 10 ml to 1000 ml. In yet another embodiment, the capacity is between 20 ml and 500 ml. In extracorporeal blood or plasma purification applications, the capacity is limited by the amount of blood which is allowed to be in the extracorporeal circuit during therapy. In one embodiment, the capacity lies in the range of from 30 ml to about 200 ml. In another embodiment, the capacity is from 30 ml to 150 ml.

Figure 3:
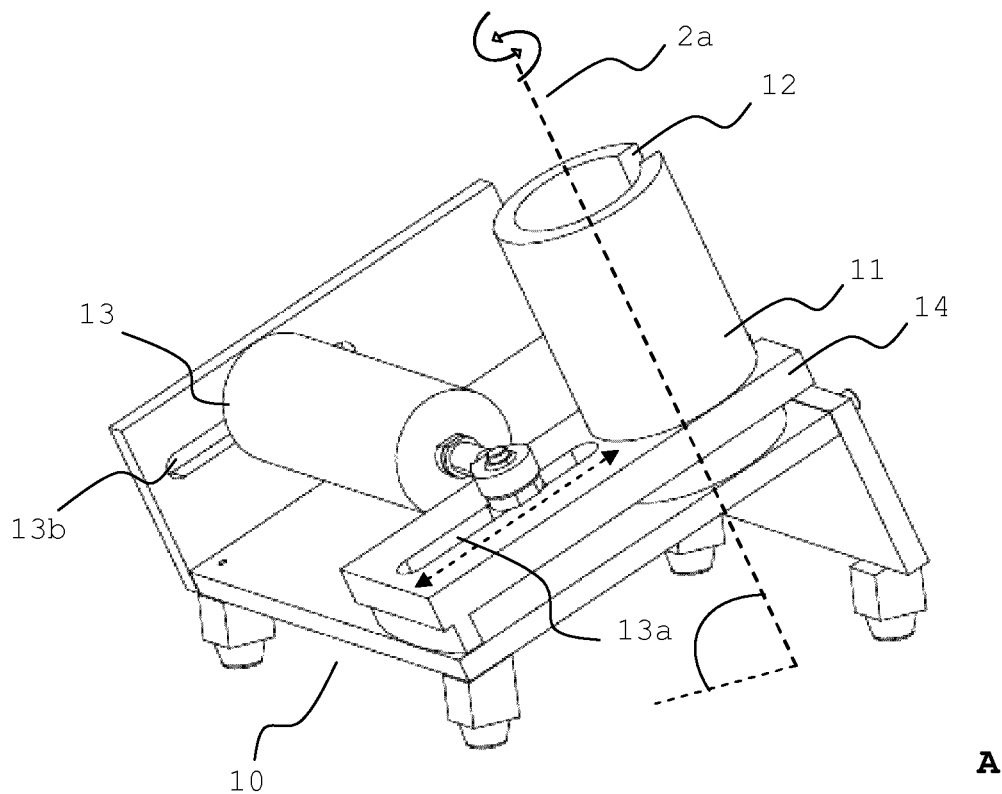
FIG. 3 shows a filling device (10) which may be used to prepare a module according to the invention. The filter module can be positioned in the mounting (11) of the device, which has a slot (12) for accommodating outlet port (9) and optionally also inlet port (7a) of the filter module. The mounting (11) is fixed to swiveling unit (14), which is in communication with a pneumatic linear vibrator (13). The vibrator (13) can be moved within slots (13a) and (13b), thereby adjusting the angular displacement of the swiveling unit (14) and the mounting (11). The swiveling unit (14) together with the mounting (11) are designed as a movable element which can be moved back and forth around essentially the longitudinal axis of the module. The filling device may be designed to allow an upright position (90°) of the filter module during filling (FIG. 3B) or an inclination of the filter module (FIG. 3A), depending on the filling process (dry or suspension) and the characteristics of the particulate material.
Figure 3:
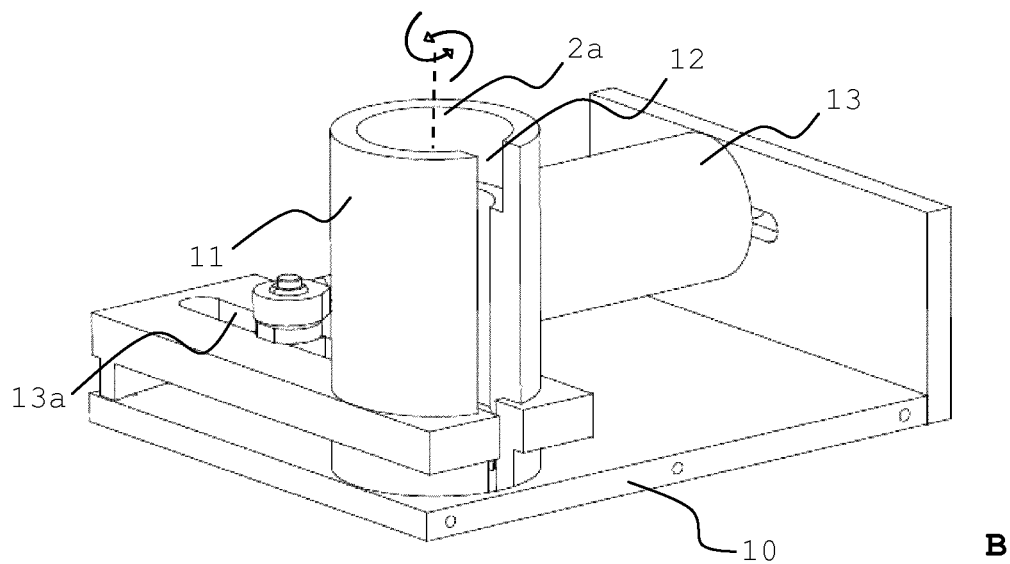
Figure 6:
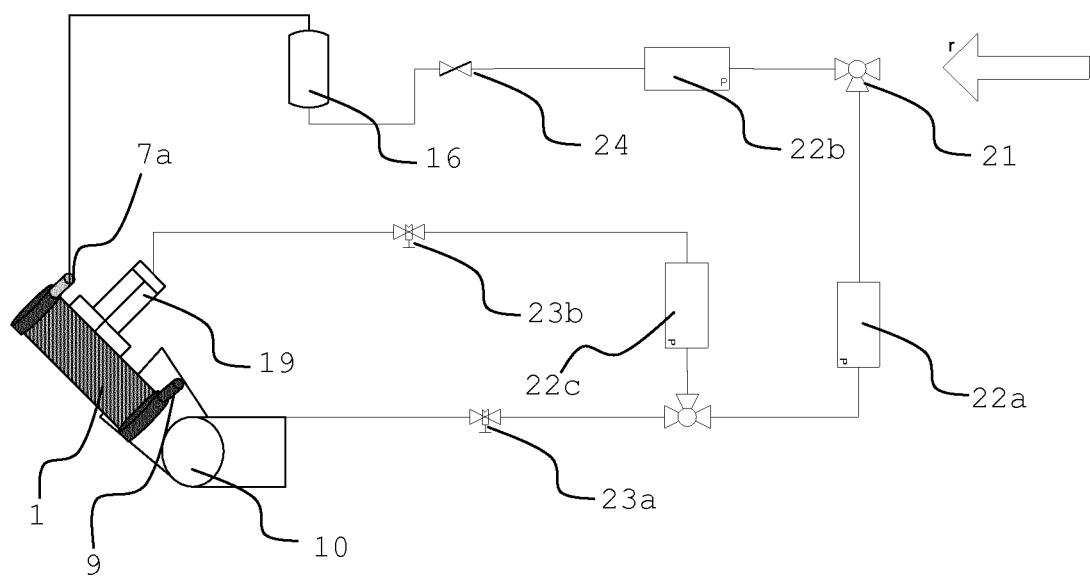
FIG. 6 shows a schematic representation of the process for the dry filling of the filter module, wherein the filter module (1) is held in an inclined position and wherein the particulate material in its dry form is introduced into the filtrate space via inlet port (7a). An impactor (19) and vibrator (10) are enabled. The dry particulate material which is stored in a feed tank (16) is introduced with compressed air from a distributor (21). Pressure within the system is regulated with the help of pressure reducers (22) and stopcocks (23) and clamp (24).

In one embodiment of the invention, the particulate material is filled into the filtrate space of a module in its dry state, wherein the filter module is held in an inclined position (see FIGS. 3A and 6). The inclination of the module allows for a smooth funneling of the material into and a homogenous distribution within the filtrate space of the module. The inclination angle of the filter module (longitudinal axis) may vary between about 30° and 80° and can be adapted to the behavior of the particulate material during transfer of the particulate material into the module. For most applications, the angle will be in the range of from 40° to 75°. In one embodiment of the invention, the module is being filled with the dry particulate material as exemplified in FIG. 6. The module (1) is positioned in the mounting (11) of the filling device (10). The mounting (11) may be designed to allow for the placement of the inlet and/or outlet of a filter module in slot (12) along the longitudinal axis of the mounting. The slot should be designed to allow for the stable positioning of the outlet (such as, for example, outlet (9)) and optionally also the inlet (such as, for example, inlet (7b)) of a module, i.e. it should be broad enough to exactly accommodate the outlet and optionally also the inlet so as to avoid any movement of the filter module (1) within the mounting (11). The module can thus be eased into the mounting and at the same time be fixed in a stable position so as to follow the rotating movements of the mounting (11) as described below. The filling device allows for an alternate clockwise and counter-clockwise rotational movement of the module around its longitudinal axis (2a) in quick succession and with a minimum total angular displacement (θ) of between 5° and 10° (see FIG. 3A and FIG. 4). The rotational movement or "shaking" of the module can, for example, be achieved with the help of a pneumatic linear vibrator (13) which may be movably mounted on the filling device (10) by positioning its ends in slots (13a) which allow shifting the vibrator horizontally on the filling device (10) (FIG. 3A).

Figure 4:
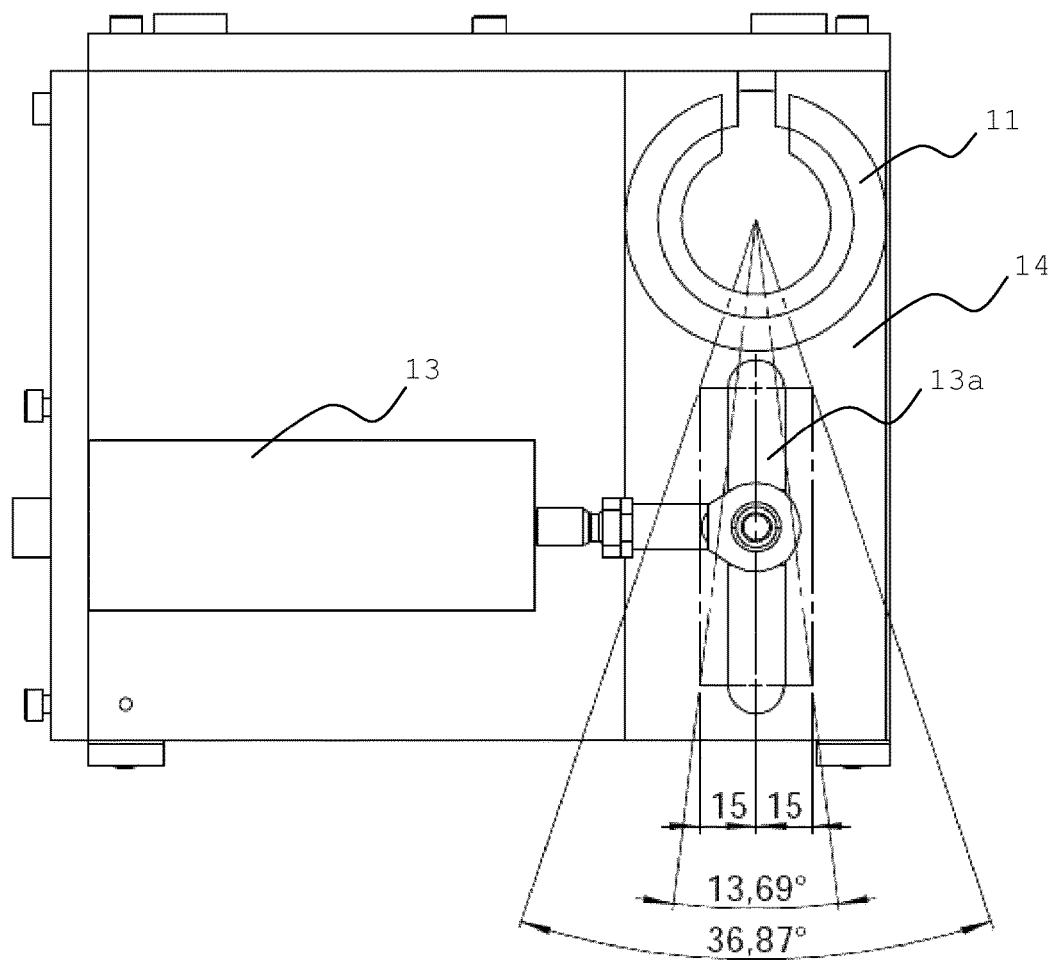
FIG. 4 shows the filling device (10) of FIG. 3 from above, wherein the possible angular displacement of swiveling unit (14) and mounting (11) and the filter module can be seen, depending on the position of the vibrator (13) in slots (13a) and (13b). The closer the vibrator (13) is positioned to the mounting (11), the larger the angular displacement will be.

One of the slots (13a) is located in a moving or swiveling unit (14) of the filling device, which is connected to the mounting (11). The Swiveling unit (14) is movably fixed to the filling device at the end where it is connected with mounting (11). Accordingly, unit (14) and mounting (11) together can be moved back and forth by the vibrator (13), resulting in a rotational movement of the module (1) positioned in the mounting (11) (FIG. 4). Like this, the angular displacement of the filter mounting (11) can be changed, depending on how close the vibrator (13) is positioned to the mounting (11). In general, a sufficient angular displacement is reached at values between about 10° and 40°, but higher values can also be used if deemed necessary. "Sufficient angular displacement" refers to such rotational movement of the mounting (11) holding the module (1) which enables the homogenous distribution of particulate material in the filtrate space with filling ratios of from 0.6 to 1.0. The frequency of the rotational movement can be varied over a broad range. It will generally lie in a range of from 1500 $min^{-1}$ to about 3000 $min^{-1}$. In one embodiment of the invention, the frequency is from 2000 $min^{-1}$ to 2800 $min^{-1}$. In addition, the module during filling is subjected to a rapping or beating movement perpendicular to the longitudinal axis of the module. For example, a pneumatic interval impactor (19) may be installed, which raps at a certain interval against the module, generally with a frequency of about 20 to 120 beats per minute. In one embodiment of the invention, about 40 to 70 beats per minute are applied. The dry particulate material is blown from a feed tank (16) into the module with compressed air. The pressure applied may vary over a certain range. It will generally lie between 0.5 and 5.0 bar, and often between 1.0 and 2.5 bar, but the pressure can easily be adapted by a person skilled in the art to the specific particulate material, the filter module and the filling device in general. The compressed air enters at an inlet (21). Pressure reducers (22), clamps (24) and stopcocks (23) may be used in order to start, guide and stop the process. The particulate material enters the filtrate space of the module at inlet (7a) and the filtrate space is filled from bottom to top. The filtrate space outlet (9) is closed.

Figure 5:
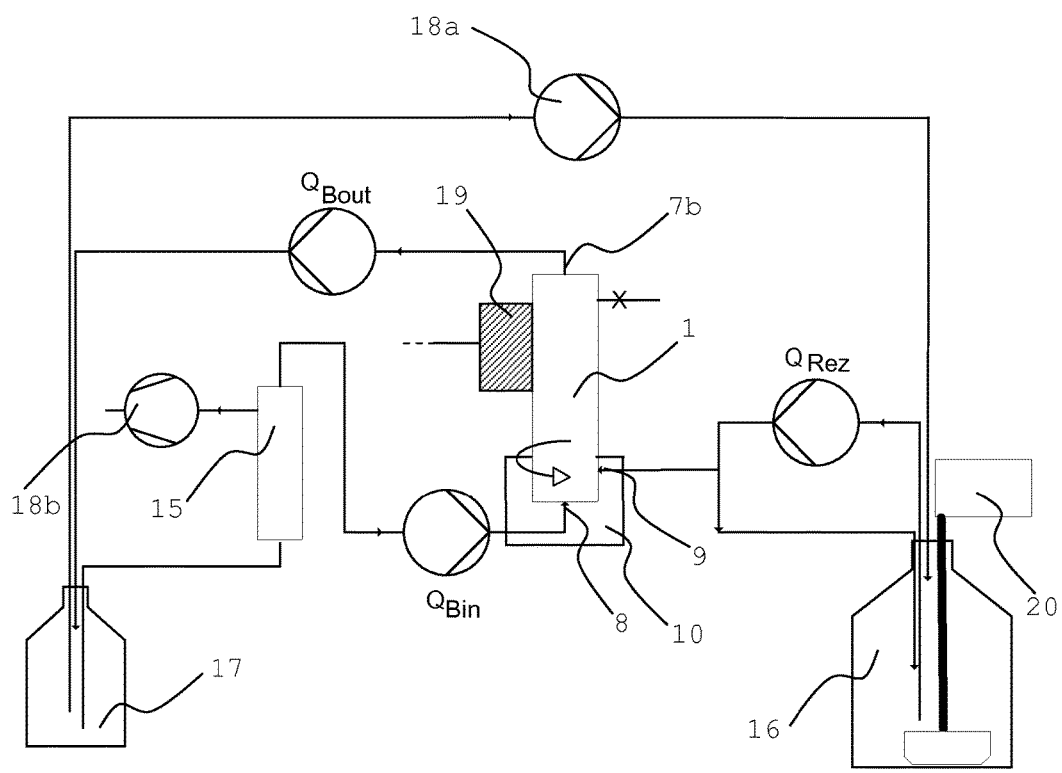
FIG. 5 shows a schematic representation of the process for the suspension filling of the filter module, wherein the filter module (1) is held in an upright (90°) position and the suspension of the particulate material is introduced into the filtrate space via outlet port (9). An impactor (19) and vibrator (10) are enabled. The suspension is pumped in ($Q_{Rez}$) from a feed tank (16) which is equipped with a stirrer (20). The solvent leaves the module at inlet port (7b), whereas the particulate material remains within the filtrate space, and the solvent is pumped ($Q_{Bout}$) into receiving tank (17). The solvent may be pumped back ($Q_{Bin}$) into the module via outlet port (8) in order to assist in the filling process, wherein a deaeration unit (15), which is in communication with vacuum pump (18b), is used to avoid the introduction of air bubbles. Inlet port (7a) is closed.

In another embodiment of the invention, the particulate material is filled into the filtrate space as a suspension. In one embodiment, the suspension of the material may be introduced into the filtrate space from top to bottom through inlet port (7a). In this case, the filling device will be arranged in a way equivalent to the device as it is used for dry material. For example, the mounting (11) will be inclined as described before for the dry material. In another embodiment of the invention, the suspension may be introduced into the filtrate space from bottom to top through outlet port (9), wherein the filter module is held in a vertical position (FIG. 3B). The filling device (10) is otherwise unchanged compared to the filling of the module with dry material. The suspension is pumped from a feed tank (16) which may be equipped with a stirrer (20) for keeping the particulate material in suspension into the filtrate space through outlet (9), wherein the particulate material is carried with the feed stream to the top of the filtrate space where it settles down (see FIG. 5). The particulate material is not able to pass the hollow fiber membrane wall and the filtrate space is filled with the particulate material from top to bottom. The solvent may leave the device through inlet port (7b) after having passed the hollow fiber membrane wall and having entered the lumen of the fibers and is pumped into a receiving tank (17) from where it is discarded and/or flows back into the feed tank (16). The solvent may be pumped from receiving tank

(17) or any other source into the module through outlet (8) in order to generate an optimal flow of the solvent through the hollow fiber lumen space of the module and to improve the rapid and homogenous filling of the filtrate space. To that end, the flow rate ($Q_{Bout}$) is advantageously set to be slightly higher than the flow rate ($Q_{Bin}$) of the solution entering the module at outlet (8). The flow rate ($Q_{Bout}$) may be set to about 200 to 700 mL/min and will often lie in the range of from 350 to 600 ml/min. The flow rate ($Q_{Bin}$) may be set to about 100 to 600 ml/min and will often lie in the range of from 200 to 500 ml/min (see also Example 2). However, the flow rates can easily be adapted to the specific particulate material, hollow fiber membrane and filter module and may deviate from the above ranges. Optimal results will be achieved with a set-up for filling the module as described before for dry particulate material, i.e. wherein the filling device provides for an alternate clockwise and counter-clockwise rotational movement as described there and wherein a knocking or rapping device is installed, such as a pneumatic interval impactor (19) which raps at a certain interval against the module, again with a frequency of about 20 to 100 beats per minute.

Various kinds of housings (2) can be used for preparing a module according to the invention, comprising those known in the art as housings for hemodialyzers, hemodiafilters or plasmafilters. Dialysis filter housings can be produced from a variety of plastic materials by a variety of processes, such as injection molding. Polycarbonates and polypropylenes are widely used in a variety of molding and extrusion applications. Poly(1,4-cyclohexylenedimethylene) terephthalate (PCT), a polyester based solely on terephthalic acid or an ester thereof and 1,4-cyclohexanedimethanol, is known in the art and is commercially available. Copolyesters of PCT can also be used. They may additionally contain dicarboxylic acids or glycols such as isophthalic acid or ethylene glycol. The polycarbonate of 4,4'-isopropylidene-diphenol (bisphenol A polycarbonate) has been used as an alternative for polyesters known in the art and is a well known engineering molding plastic. Polymers containing 2,2,4,4-tetramethyl-1,3-cyclobutanediol have also been generally described in the art. Housings may also be prepared from polyester compositions made from terephthalic acid, or an ester thereof, or mixtures thereof, 2,2,4,4-tetramethyl-1,3-cyclobutanediol, and 1,4-cyclohexanedimethanol. It is also possible to use housing made of PVC or uPVC, especially for bioprocessing applications. The dimensions of the housings (2) which can be used in according to the present invention can vary over a broad range, as long as the critical fiber allocation in the cylindrical filter housing is kept in a range of between 15% and 70%. For the modular design of tangential-flow filtration configurations in bioprocessing applications, for example, it is generally possible to increase the size of a module according to invention on the basis of several standard scale-up parameters which need to be considered and kept constant during the operation and which are known in the art (Lee et al. 2011: "Membrane Separation Theoretical and Applicable Considerations for Optimum Industrial Bioprocessing"; J. Bioproces. Biotechniq., Volume 1, Issue 2), comprising the inlet and outlet pressures, the tangential flow velocity, the flow channel sizes, the membrane characteristics such as its type and the feed stream properties. Often, a scale up will be done according to achieve a constant flux rate which will involve increasing the surface area of the filtration module and keeping constant a given fiber allocation to maintain constant flux rate at the larger scale. For medical applications, especially extracorporeal therapies, the size of the filter module and the housing is limited by the parameters which are generally known to a person with skill in the art.

The filter modules of the invention can be sterilized by methods which are known in the art, such as chemical sterilization, steam sterilization or gamma radiation for wet modules. For dry modules, e-beam sterilization, dry heat or EtO sterilization are possible sterilization methods. The choice of the sterilization method will otherwise have to be adapted to the particulate material in the module.

EXAMPLES

Example 1

Preparation of a Filter Module Comprising Hollow Fibers and Particulate Material in the Filtrate Space (Dry Filling)

Standard Plasmylane® 6 plasmafilters were used to prepare a filter module with active particulate material on the filtrate side of the module. The Plasmylane® filter module possesses connectors at the blood side and the filtrate side according to ISO 8637:2004. The fibers are made from a combination of PEAS and PVP and have an inner diameter of 320 μm and a wall thickness of 50 μm. Their effective length is 220 mm. The fibers are crimped with a depth of 2.0 mm. The total membrane surface area is 0.6 m². The housing is made from polycarbonate (PC) and has a usable volume (filtrate space), $V_{FS}$, of 189 ml, a diameter of 39.6 mm and a total length of 217.3 mm. The potting material consists of polyurethane. The plasmafilter can be run with blood flow rates in the range of about 80-250 mL/min.

Two Plasmylane® 6 plasmafilters were filled with Reli-Zyme™ EXE 135 (Resindion S.R.L., Italy) beads having residual moisture of 15-25%. The filter was filled in accordance with the filling set-up as shown in FIG. 6.

The Plasmylane® 6 plasmafilters were weighed to identify the initial mass of the filters. The filters were then installed in the mounting (11) of the filling device (10) and a pneumatic interval impactor (19) (Netter Druckluft-Intervallklopfer PKL 190, Netter GmbH, Germany) was attached to the filter module. The mounting (11) was set to an inclination of 70°. Outlet port (9) was closed and inlet port (7a) was opened. Blood outlet port (8) was also opened. A pneumatic linear vibrator (Netter Druckluft-Kolbenvibrator NTK 15x, Netter GmbH, Germany) was connected to pressure reducer (22a) and set to 6.0 bar corresponding to a frequency of about 2544 min⁻¹. Stopcock (23a) and clamp (24) remain closed. Pressure reducer (22b) is set to 1.5 bar. 65 g of the beads (dry weight) were added to the feed tank (16). The feed tank was connected to the system in a way to allow perfusion with air from bottom to top and was further connected to inlet port (7a). Stopcock (23a) was opened and the pneumatic linear vibrator was started. Then stopcock (23b) was opened and the pneumatic interval impactor was started with a pressure of 4.5 bar corresponding to 54 beats per minute. Clamp (24) was opened and the beads were blown by compressed air (1.5 bar) into the filtrate side of the filters from top to bottom. The filling process was stopped after 237 seconds and 217 seconds, respectively, when the filters were completely filled with beads as judges upon visual inspection and increase in pressure within the system. At that time the clamp was again closed and the pressure was released. The vibrator and the impactor were stopped. The filter modules were removed from the filling device and dried over night until the mass did not change any more. Then the mass of the filter modules was taken in order to determine the amount of beads which were deposited in the filtrate space of the modules. Filter module 1 was filled with 45.9 g of the beads, Filter module 2 with 45.2 g of the beads.

The tapped densities of the ReliZyme™ EXE 135 and ReliZyme™ EXE 148 dry beads were determined in order to calculate the filling ratio for the modules according to DIN ISO 3953. The tapped density which was determined for dry ReliZyme™ EXE 135 beads is 0.40 g/ml. The tapped density which was determined for dry ReliZyme™ EXE 148 beads is 0.50 g/ml. The volume $V_{PM}$ for Filter module 1 is thus 114.75 ml, for Filter 2 it is 113.00 ml. With $V_{FS}$ being 189 ml, the filling ratios for Filter 1 and 2 are 0.61 and 0.60, respectively.

Example 2

Preparation of a Filter Module Comprising Hollow Fibers and Particulate Material in the Filtrate Space (Suspension Filling)

Standard Plasmylane® 6 plasmafilters as described in Example 1 were used. The filling of the filters was done according to FIG. 5, i.e. the filling was done from bottom to top. The mounting (11) was in an upright position (see FIG. 3B), i.e. it was set to 90°. The suspension entered the filtrate space at outlet port (9). The filling device including the pneumatic linear vibrator and the pneumatic interval impactor were otherwise set to values as described in Example 1 (6.0 bar and 4.5 bar, respectively). $Q_{Bin}$ was set to 350 mL/min, $Q_{Bout}$ to 550 mL/min. The pumps were started at the same time. $Q_{Rez}$, which defines the flow speed of the suspension from the feed tank to the module, was set to 550 mL/min, finally resulting in a filtration flow rate of 200 mL/min.

Two different types of particulate material were used: ReliZyme™ EXE 135 (Resindion S.R.L., Italy) beads having an average particle size of about 200 μm and ReliZyme™ EXE 148 (Resindion S.R.L., Italy) beads having an average particle size of about 60 μm. Two of the filters (Filters 3, 4, see Table I) were filled with beads which were treated for subsequent CT measurements (Example 4). A suspension of the beads was prepared. A total initial volume of 5000 mL with approximately 50 g of the beads and a resulting concentration of about 0.01 g/mL was provided, respectively. A stirrer (20) was installed for keeping the beads in suspension.

In a first step, the filters were filled on the blood side and the filtrate side with degassed RO water under avoidance of air bubbles. The pneumatic interval impactor as well as the pneumatic linear vibrator was connected to compressed air and the pumps were started with flow rates given above. The beads were fed into the filtrate space at the bottom of the device and quickly settled at the top of it, followed by the gradual filling of the module with beads from the top until the filtrate space was completely filled. The process was then stopped and the unused beads remaining in the feed tank were dried and weighed. The results for the filters which were filled according to Example 2 are shown in Table I.

TABLE I

| Filter No. | m [g] filter without particles | m [g] filter with H$_2$O | Beads used | m [g] beads (dry) used | p [bar] vibrator | p [bar] impactor | t [min] | m [g] beads within module (dry) |
|---|---|---|---|---|---|---|---|---|
| 1 | 132.28 | 381.67 | EXE 148 | 64.99 | 6 | 4.5 | 60 | 41.13 |
| 2 | 132.93 | 381.25 | EXE 148 | 53.11 | 6 | 4.5 | 36 | 40.97 |
| 3 | 132.45 | 382.31 | EXE 135 | 70.37 | 6 | 4.5 | 123 | 48.27 |
| 4 | 132.35 | 382.08 | EXE 148 | 83.25 | 6 | 4.5 | 42 | 53.27 |
| 5 | 132.41 | 382.82 | EXE 135 | 50.08 | 6 | 4.5 | 63 | 41.70 |
| 6 | 132.53 | 382.11 | EXE 135 | 50.95 | 6 | 4.5 | 38 | 42.01 |

Filters 1, 2, 5 and 6 were filled with the beads as shown in Table I. Filters 3 and 4 differed with regard to the beads, which had been treated with HI (hydrogen iodide) before they were filled into the module. The treatment with HI was done for being able to control the beads' distribution within the module (see Example 4).

Filling ratios were determined as described before. The tapped densities of the ReliZyme™ EXE 135 and ReliZyme™ EXE 148 suspended beads were determined in order to calculate the filling ratio for the modules according to DIN ISO 3953. The tapped density which was determined for suspended ReliZyme™ EXE 135 beads is 0.28 g/ml. The tapped density which was determined for dry ReliZyme™ EXE 148 beads is 0.33 g/ml. The volumes $V_{PM}$ for Filters 1 to 6 are thus 124.64 ml, 124.15 ml, 172.39 ml, 161.42 ml, 148.93 ml and 150.04 ml, respectively. With $V_{FS}$ being 189 ml, the filling ratios for Filters 1 to 6 are 0.66, 0.66, 0.91, 0.85, 0.79 and 0.79, respectively.

Example 3

Comparative Example

Comparative tests were done for showing the difference in filling approaches according to the state of the art and according to the present invention. Therefore, Plasmylane® 6 plasmafilters were filled with dry beads or beads in suspension as described in Examples 1 and 2, respectively. However, the pneumatic interval impactor and the pneumatic linear vibrator of the filling device were not enabled. The filling process was terminated in each case when the module was completely filled upon visual control and/or no further particles could be introduced into the filtrate space of the module, resulting in a pressure increase in the system. The amount of beads which could be filled into the modules was determined as described before. The density used for the reference Examples without enabled vibrator and compactor is a "bulk density", which has been determined to be also 0.40 g/ml for dry ReliZyme™ EXE 135, 0.27 g/ml for wet ReliZyme™ EXE 135, 0.40 g/ml for wet ReliZyme™ EXE 148 and 0.28 g/ml for wet ReliZyme™ EXE 148. Table II summarizes the results of the filling experiments.

TABLE II

| | Method | m[g] beads introduced | Filling ratio $\frac{V_{PM}(ml)}{V_{FS}(ml)}$ |
|---|---|---|---|
| Suspension filling | Example 2 (ReliZyme ™ EXE 135) | 41.15 | 0.77 |
| | Example 2 (ReliZyme ™ EXE 135), vibrator and impactor disabled | 8.94 | n.d. |
| Dry filling | Example 1 (ReliZyme ™ EXE 135) | 45.16 | 0.60 |
| | Example 1 (ReliZyme ™ EXE 135), vibrator and impactor disabled | 5.45 | n.d. |

Example 4

CT Control of Filter Modules with Particulate Material in Filtrate Space

In addition to determining the absolute volume of the particulate material which can be accommodated according to the invention, and the filling ratio, it is necessary to control the homogeneity of the bead distribution within the device. Only a homogenous distribution of the particulate material provides for optimal flow characteristics (internal filtration) and high efficiency of the filter modules in the respective applications. To that end, CT scans (X-ray computed tomography) of filled modules were prepared to control the results of the fillings. Again, standard filling procedures were used according to the state of the art and compared to the filling process as described in the present application (see Ex. 3).

The beads (ReliZyme™ EXE 135), before filling them into the filtrate space of standard Plasmylane® 6 plasmafilters as described in Example 1, were treated with HI wherein iodine is added to the epoxy groups of the beads. The treatment increases the beads' absorption of x-rays, thus making them better visible in the CT scanning experiments. In the scans, dark portions correspond to fewer or no beads, whereas lighter or white portions show the presence of beads as X-rays are being absorbed by the material.

The beads were filled into the filtrate space in their dry form (residual moisture: >1.5%) until the filtrate space was completely filled and no further material could be introduced. In a first experiment, the vibrator and impactor were disabled. However, a frequent manual tapping of the housing was done in order to avoid that the material got stuck already in the upper part of the device and to allow the introduction of particles into essentially the complete filtrate space of the device, thus allowing a comparison between devices prepared according to the invention and according to prior art approaches. Without any frequent tapping, manual or otherwise, less material can be introduced (see Ex. 3). The beads were introduced at a pressure of 1.0 bar. Like that, 37 g of the beads could be introduced into the filtrate space of the device before the module had been completely filled, based on visual control on a pressure increase in the system.

In a second experiment, the vibrator was enabled and the filling was done according to the invention. The beads (residual moisture: 27.18%) were introduced at a pressure of 1.5 bar. The pneumatic linear vibrator was set to 6.0 bar, corresponding to a frequency of about 2500 min$^{-1}$. The impactor was not enabled. Like that, 48 g of the beads could be introduced into the filtrate space of the device before pressure increased in the system.

Figure 7A:
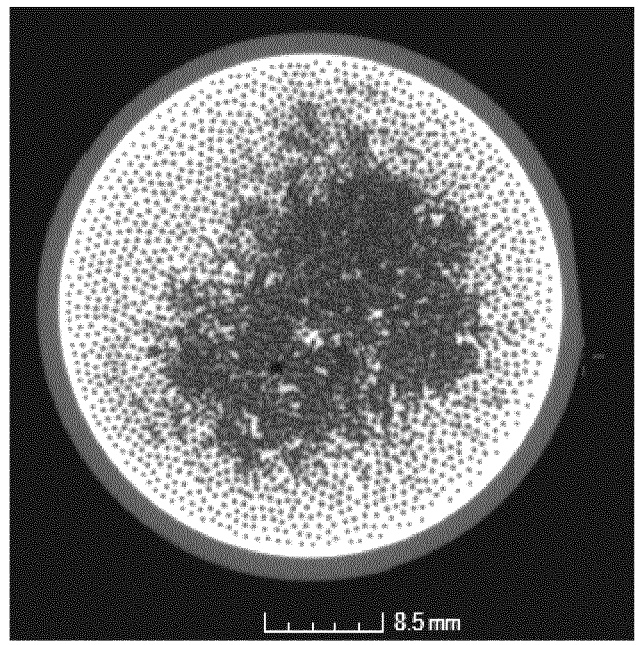
FIG. 7A shows the CT scans of a module which has been filled with dry particulate material according to Example 4 and according to standard filling methods without vibrator and/or impactor, but with a manual tapping against the housing in order to allow the beads to be introduced before the filtrate space until no more beads could be filled in and upon visual control the filtrate space was completely filled with the material. Dark portions can be observed mainly in the central portion of the module where significantly fewer or no beads are deposited than at the periphery, where white color represents the presence of beads.
Figure 7B:
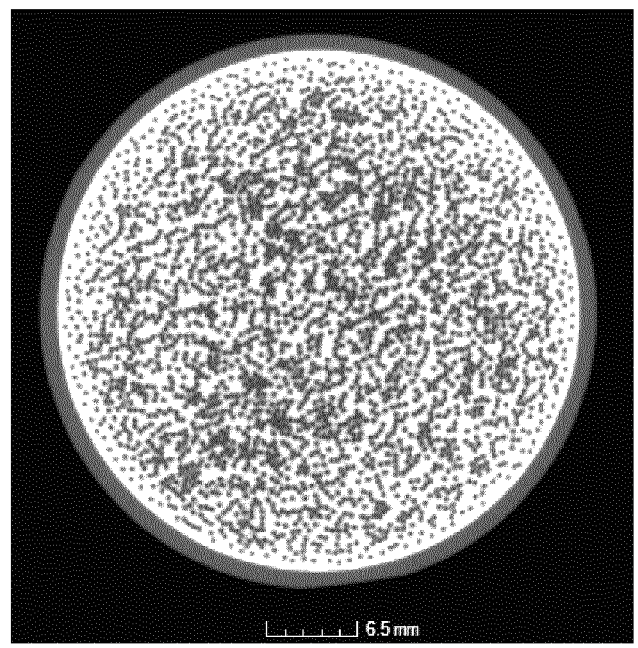
FIG. 7B shows the CT scans of a module which has essentially been filled according to the present invention, i.e. in the presence of a pneumatic linear vibrator, however in the absence of an impactor (see Example 4). The beads (white) are distributed in a significantly more homogenous manner than in FIG. 7A over the complete section of the module.
Figure 8A:
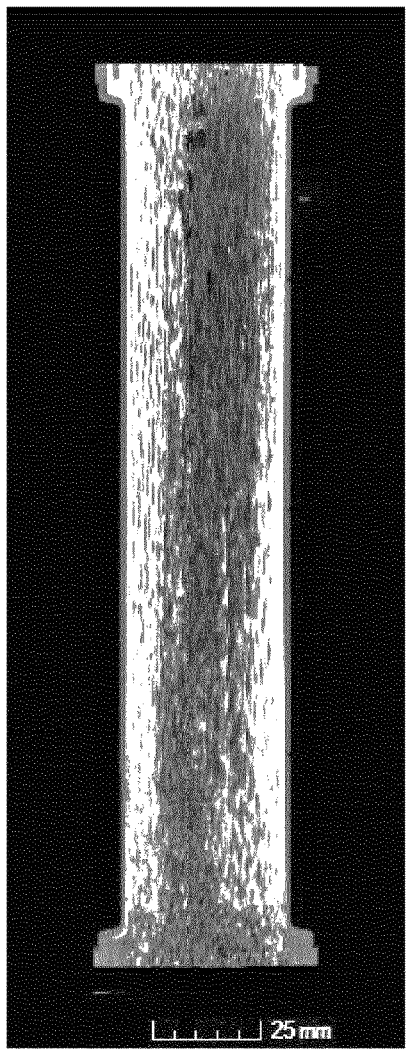
FIG. 8A (standard filling method) shows the defects which were visible already in the cross-section also over the full length of the module.
Figure 8B:
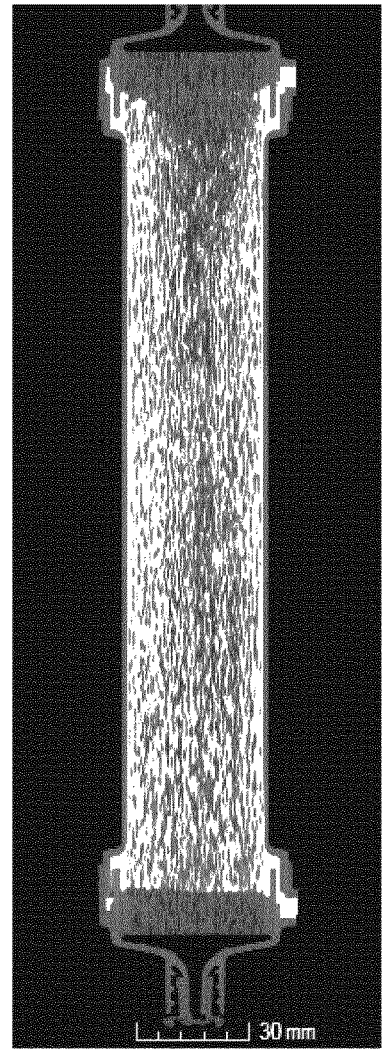
FIG. 8B (filling according to the invention), in contrast, shows that the beads are evenly and homogenously distributed over essentially the full length of the module and that no defective portions exist which would negatively impact the efficiency of the module.
Figure 9:
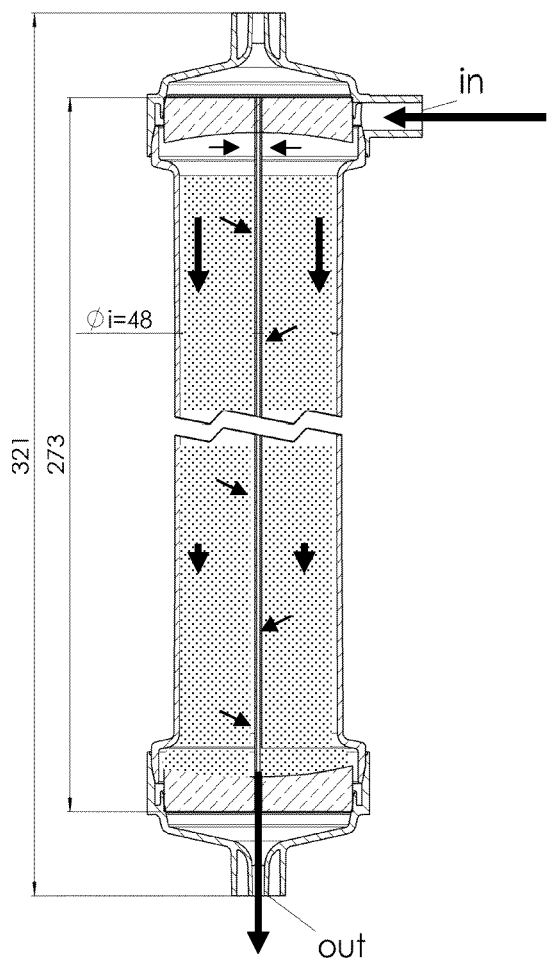
FIG. 9 shows a schematic representation of a module according to the invention, including possible parameters of the housing, wherein the fluid to be treated enters the device through an inlet port which is in communication with the filtrate space of the module. The treated fluid leaves the module after passage of the hollow fiber membrane wall through the outlet port which is in communication with the hollow fiber lumen space.
Figure 10:
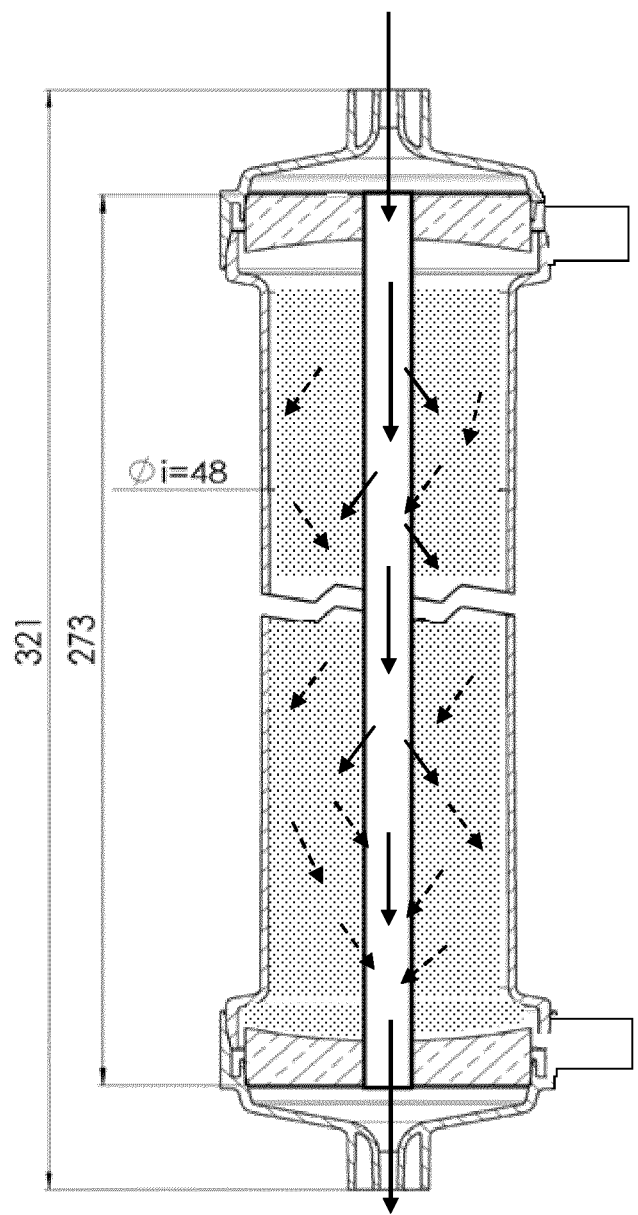
FIG. 10 shows a schematic representation of a module according to the invention, including possible parameters of the housing, wherein the fluid to be treated enters the device through an inlet port which is in communication with the hollow fiber lumen space of the module. The fluid or portions thereof pass the membrane wall and get into contact with the particulate material in the filtrate space, from where the treated fluid re-enters the hollow fiber lumen space and eventually leaves the module through the outlet port which is in communication with said lumen space.

Both filters were then filled with water. The introduction of air was avoided. The filters were emptied on the blood site and submitted to CT scans. FIGS. 7 and 8 show the results of the CT scans. FIGS. 7A and 8A relate to the filter device which was filled without vibrator and impactor, but with a constant and vigorous manual tapping. Strikingly, even though a quite significant amount of beads could be filled into the device without the help of a filling device (10) according to the invention, the distribution of the beads within the device turned out to be very inhomogeneous. Especially in the center portion of the device defects or voids can be seen where significantly less beads are located than at the periphery of the device. In such device, the treatment of a fluid would be inefficient because the fluid would preferably flow through the less populated portions, thus avoiding the contact with the majority of the beads. FIGS. 7B and 8B show the results for the filter which was filled according to the invention, in the presence of a pneumatic linear vibrator. As can be seen, even though the impactor was not used, the distribution of the particulate material within the filtrate space has become very homogenous. No significant defects can be seen there. Imperfections in homogeneity in the upper quarter of the device can be avoided by additionally applying an impactor and by carefully determining the end point of the filling process.

Example 5

CT Control of Filter Modules Prepared According to the Invention

CT scans of filter modules were prepared essentially as described in Example 4. This time, however, the modules were prepared with ReliZyme™ EXE 135 and ReliZyme™ EXE 148 beads, respectively, by using the suspension filling and dry filling process in the presence of both the pneumatic linear vibrator and the pneumatic interval impactor (see Ex. 1 and Ex. 2). Standard Plasmylane® 6 plasmafilters as described in Example 1 were used. Table III provides for the amount of beads which could be introduced into the filtrate space of the respective filter modules and the resulting filling ratios.

TABLE III

| Filter No. | Beads | Filling Method | m [g] beads introduced | Filling ratio $\frac{V_{PM}(ml)}{V_{FS}(ml)}$ |
|---|---|---|---|---|
| 1 | ReliZyme ™ EXE 135 | suspension | 48.27 | 0.91 |
| 2 | ReliZyme ™ EXE 148 | suspension | 53.27 | 0.85 |
| 3 | ReliZyme ™ EXE 135 | dry | 56.83 | 0.75 |
| 4 | ReliZyme ™ EXE 148 | dry | 83.17 | 0.88 |

Figure 11:
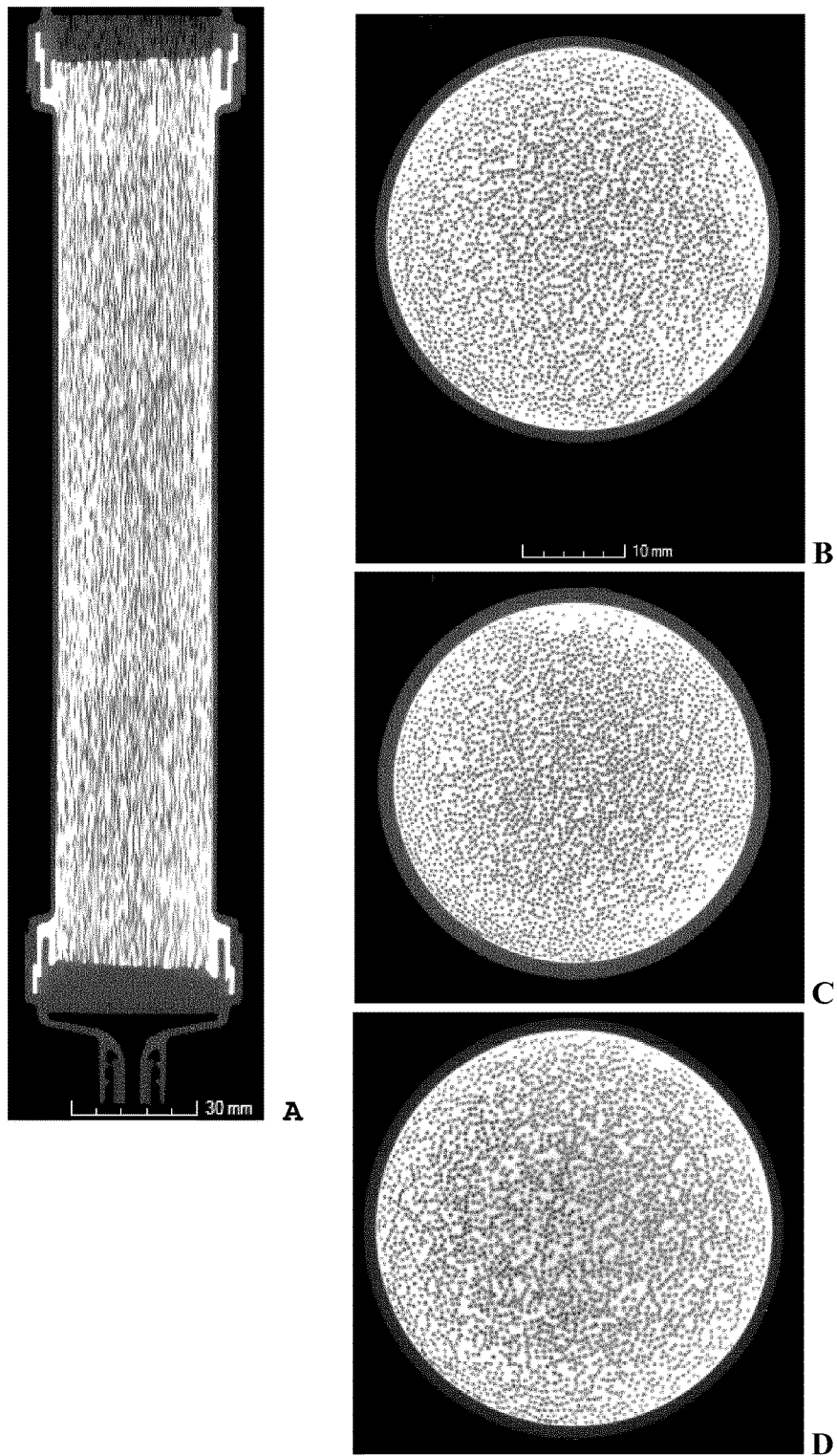
FIG. 11 shows CT scans of cross-sections through hollow fiber filter module 2 of Example 5. The hollow fibers can be seen as dark dots which are more or less evenly distributed over the cross-section. White portions represent beads.
Figure 12:
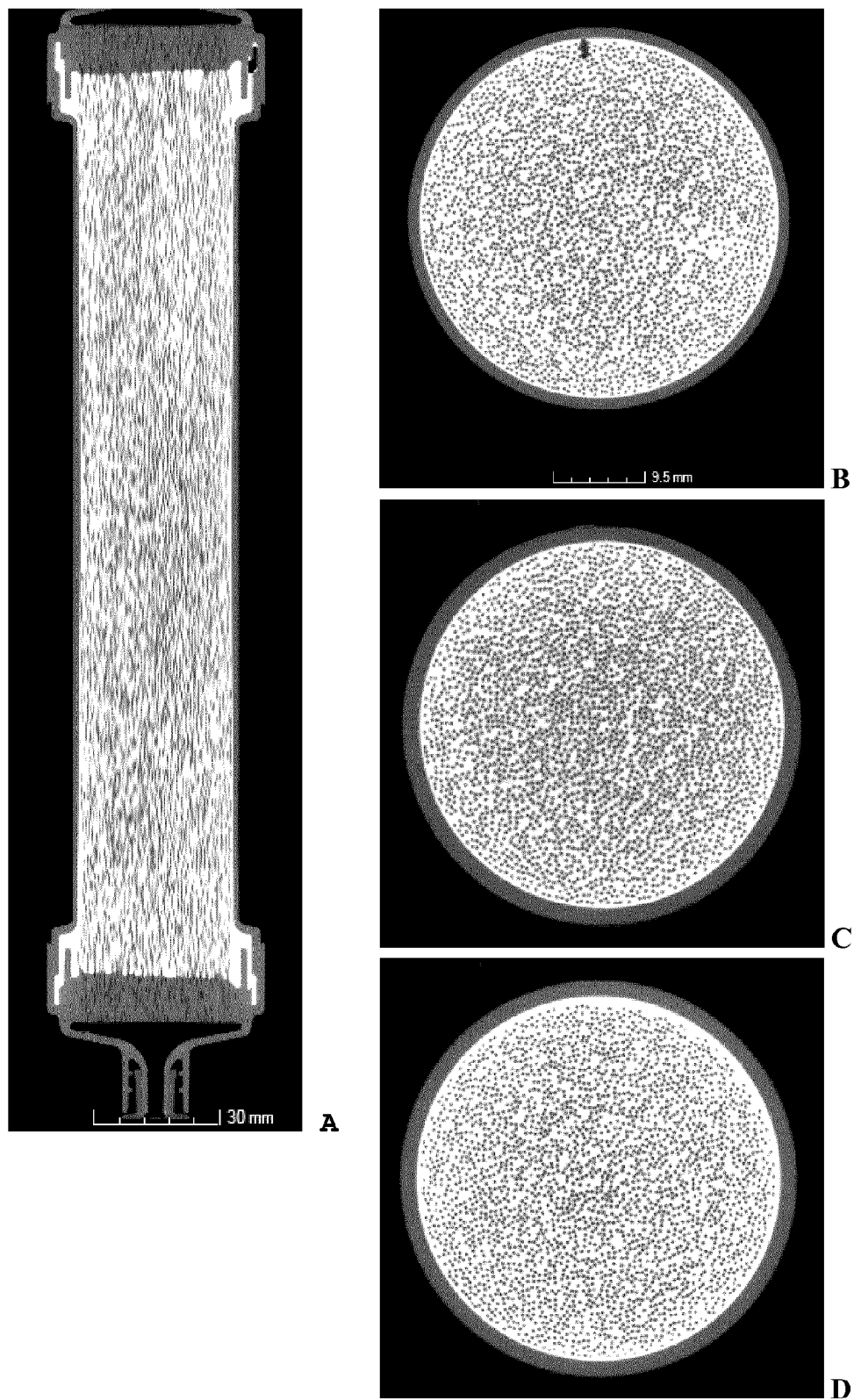
FIG. 12 shows CT scans of cross-sections through hollow fiber filter module 4 of Example 5. The hollow fibers can be seen as dark dots which are more or less evenly distributed over the cross-section. White portions represent beads.

CT scans of filters 2 and 4 are exemplarily shown in FIGS. 11 and 12, respectively. It is obvious that the homogeneity could be further optimized over the full length of the device by applying both the vibrator and the impactor. Any defects in the upper quarter of the modules which could still be seen in the CT scans of Example 4 are no longer visible in the modules which were prepared as described here. Also, the average filling ratio could be further improved.

The invention claimed is:

1. A hollow fiber membrane module for the treatment of fluids, comprising
    (a) a cylindrical filter housing;
    (b) a bundle of essentially parallel hollow fiber membranes distributed longitudinally within the cylindrical filter housing, wherein the hollow fiber membranes comprise open ends that are in fluid communication with a distribution space and with a collection space, and wherein the open ends are embedded in a sealing compound such that the open ends of the hollow fibers extend through the sealing compound;
    (c) a filtrate space, which is closed off from the distribution space and the collection space and a lumen space of the hollow fiber membranes;
    (d) an inlet means for feeding the fluid into one of the filtrate space and the distribution space which is in fluid communication with the lumen side of the hollow fiber membranes, the filtrate space being optionally interconnected with one of the inlet means and an outlet means;
    (e) a first outlet means for removing the treated fluid from the cylindrical filter housing, said first outlet means being in fluid communication with the collection space, and optionally a second outlet means for removing treated fluid from the filtrate space;
    wherein a fiber allocation in the cylindrical filter housing is between 15% to 70%; and
    wherein the filtrate space is homogenously populated with a particulate material being capable of interacting with at least one component of the fluid with a filling ratio of between 0.6 and 1.0, wherein the filling ratio is the volume in ml of the maximal amount of particulate material which can be accommodated in the filtrate space of a given hollow fiber membrane module ($V_{PM}$) and the utilizable volume in ml of the filtrate space of said module ($V_{FS}$):

$$\text{Filling ratio} = \frac{V_{PM}(\text{ml})}{V_{FS}(\text{ml})}$$

wherein $V_{PM}$ resents the volume of the particulate material which can be accommodated in the filtrate space of the module, and $V_{FS}$ represents the utilizable filtrate space, and wherein $V_{PM}$ is calculated from $$V_{PM}(\text{ml}) = \frac{m_{PM}(g)}{\rho(g/\text{ml})}$$

wherein $m_{PM}$ represents the amount of particulate material which can be accommodated in the filtrate space of the module and p represents the tapping density of the particulate material according to DIN ISO 3953.

2. A module according to claim 1 wherein the particulate material consists of particles having a diameter of between 1 μm to 400 μm.

3. A module according to claim 1 wherein the hollow fiber membrane is a plasma separation membrane.

4. A module according to claim 1 wherein the hollow fiber membrane is a membrane having entrapped therein functionalized or active particulate material.

5. A module according to claim 1 wherein the fluid enters the module at the inlet means which is in fluid communication with the filtrate space.

6. A module according to claim 1 wherein the fluid enters the module at the inlet means which is in fluid communication with the lumen side of the hollow fiber membranes.

7. A module according to claim 1 wherein the particulate material is selected from a group of materials comprising anion exchangers, cation exchangers, hydrophilic adsorbents, hydrophobic adsorbents, immunoadsorbents, adsorbents comprising affinity ligands attached thereto and mixtures thereof.

8. A module according to claim 1 wherein the particulate material is selected from a group of polymeric adsorbents comprising nylon polymers, polymers of acrylic acid, methacrylic acid, co-polymers of ethylene and maleic acid anhydride, styrenic polymers, polydivinylbenzene polymers, styrenedivinylbenzene copolymers, or mixtures thereof.

9. A module according to claim 7 wherein the anion exchangers are based on polystyrene or styrene-divinylbenzene and which may be unmodified or modified with sulphonic acids, polyamines or quaternary or tertiary amines or on a copolymer of styrene and divinylbenzene carrying active groups such as quaternary ammonium groups, dimethylethanolamine groups, dimethylethanolbenzyl ammonium groups, benzyltrialkyl ammonium groups, benzyldimethyl(2-hydroxyethyl) ammonium and/or trimethylbenzyl ammonium functional groups.

10. A module according to claim 7 wherein the cation exchangers are based on matrices of agarose, cellulose, dextran, methacrylate, polystyrene or polyacrylic acid.

11. A module according to claim 7 wherein the hydrophobic adsorbents are selected from a group consisting of carbonaceous adsorbents, polymer adsorbents and hydrophobic silica.

12. A module according to claim 1 wherein the particulate material is provided in the form of beads.

13. A module according to claim 12 wherein the beads are selected from the group consisting of silica beads, magnetic beads, and hydrophilic polymer gel beads.

14. A module according to claim 1 wherein the fluid is whole blood, plasma, or peritoneal fluid.

15. A module according to claim 1 wherein one or more enzymes are coupled to the particulate material.

16. A module according to claim 1 wherein a hemodialyzer is connected thereto in series.

17. A module according to claim 2 wherein the fiber allocation in the cylindrical filter housing is between 20% and 55%.

18. A module according to claim 1 wherein the hollow fiber membrane is a high cut-off membrane.

19. A module according to claim 1 wherein the hollow fiber membrane is a protein separation membrane.

* * * * *